US010265348B2

(12) United States Patent
Soley Astals et al.

(10) Patent No.: US 10,265,348 B2
(45) Date of Patent: Apr. 23, 2019

(54) COSMETIC AND/OR PHARMACEUTICAL COMPOSITION CONTAINING A BACTERIAL EXTRACELLULAR PRODUCT FROM PSEUDOALTEROMONAS ANTARCTICA, AND USE THEREOF

(71) Applicant: Lipotec, S.A.U., Gava, Barcelona (ES)

(72) Inventors: Albert Soley Astals, Barcelona (ES); Núria Almiñana Domènech, Barcelona (ES); Antonio Vicente Ferrer Montiel, Alicante (ES); Marc Esplugas Gonzalez, Barcelona (ES)

(73) Assignee: Lipotec S.A.U., Gava, Barcelona (ES)

( * ) Notice: Subject to any disclaimer, the term of this patent is extended or adjusted under 35 U.S.C. 154(b) by 4 days.

(21) Appl. No.: 15/522,564

(22) PCT Filed: Nov. 2, 2015

(86) PCT No.: PCT/EP2015/075485
§ 371 (c)(1),
(2) Date: Apr. 27, 2017

(87) PCT Pub. No.: WO2016/066857
PCT Pub. Date: May 6, 2016

(65) Prior Publication Data
US 2017/0333491 A1    Nov. 23, 2017

(30) Foreign Application Priority Data
Oct. 31, 2014   (EP) .................................... 14382430

(51) Int. Cl.
| A61K 8/99  | (2017.01) |
| A61Q 5/00  | (2006.01) |
| C12R 1/00  | (2006.01) |
| A61K 35/74 | (2015.01) |
| A61Q 19/00 | (2006.01) |
| A61Q 19/08 | (2006.01) |

(52) U.S. Cl.
CPC ................ *A61K 35/74* (2013.01); *A61K 8/99* (2013.01); *A61Q 5/008* (2013.01); *A61Q 19/008* (2013.01); *A61Q 19/08* (2013.01); *C12R 1/00* (2013.01)

(58) Field of Classification Search
CPC .......... A61K 35/74; A61K 8/99; A61Q 5/008; A61Q 19/008; A61Q 19/08; C12R 1/00; C12R 1/01
See application file for complete search history.

(56) References Cited

U.S. PATENT DOCUMENTS

| 2003/0110518 A1 | 6/2003 | Houseknecht et al. |
| 2009/0221558 A1 | 9/2009 | Blaskovich et al. |
| 2011/0195103 A1* | 8/2011 | Perez Arcas ............ A61K 8/73 424/401 |
| 2013/0302261 A1 | 11/2013 | Courtois et al. |

FOREIGN PATENT DOCUMENTS

| EP | 1402898 B1 | 3/2004 |
| WO | WO 03/040118 A1 | 5/2003 |
| WO | WO 2010/043346 | 4/2010 |
| WO | WO 2012/072245 | 6/2012 |

OTHER PUBLICATIONS

A. de la Maza, J. L. Parra, M. Sabes, F. Congregado, N. Bozal, and J. Guinea, "Glycoprotein Excreted by Pseudoalteromonas antarctica NF3 as a Coating and Protective Agent of Liposomes against Sodium Dodecyl Sulfate", Langmuir 1998, 14, 42-48. (Year: 1998).*
Pappas, "Epidermal Surface Lipids", Dermato-Endocrinology vol. 1, pp. 72-76 (2009).
Nieman, et al., "Development and Homeostasis of the sebaceous gland", Seminars in Cell & Developmental Biolosy vol. 23, pp. 928-936 (2012) (Abstract only).
Smith, et al., "Sebaceous gland lipids: friend or foe?" Journal of Lipid Research, vol. 49, pp. 271-281 (2008).
Bednarek, et al, "Potent and Selective Peptide Agonists of a-Melanocyte Stimulating Hormone (αMSH) Action at Human Melanocortin Receptor 5; their Synthesis and Biological Evaluation in vitro", Chem. Biol. Drug. Des., vol. 69, pp. 350-355 (2007) (Abstract only).
Thibotout, et al., "The Melanocortin 5 Receptor is Expressed in Human Sebaceous Glands and Rat Preputial Cells", J. Invest. Dermatol. vol. 115, pp. 614-619 (2000).
Zhang et al, "Melanocortin-5 receptor: A marker of human sebocyte differentiation", Peptides vol. 27, pp. 413-420 (2006).
Parchami, et al., "Effect of ovariectomy and chronic sex steroid administration on rabbit skin", Global Veterinaria, vol. 4(6), pp. 610-615 (2010).
Wilkinson, "Harry's Cosmeticology", Seventh edition, Moore R.J., ed. Longman House, Essex, GB, pp. 50-73 and 757-799 (1982).
Schaab, "Impregnating Fabrics with Microcapsules," HAPPI, pp. 84-86 (1986).
Nelson, "Application of microencapsulation in textiles", Int. J. Pharm., vol. 242(1-2), pp. 55-62 (2002).
Hipler, "Biofunctional Textiles and the Skin" Curr. Probl. Dermatol. vol. 33, eds. S. Karger AG, Basel, Switzerland, pp. 1-36 (2006).
Malcolm et al., "Controlled release of a model antibacterial drug from a novel self-lubricating silicone biomaterial," J. Cont. Release, vol. 97(2), pp. 313-320 (2004).
Gottschalck, et al., CTFA International Cosmetic Ingredient Dictionary & Handbook, 12th Edition, pp. 3040-3065 (2008).
Wang, et al., "Cloning, expression, purification, and characterization of glutaredoxin from Antarctic sea-ice bacterium Pseudoalteromonas sp. AN178," Biomed Research International, vol. 2014/246871, pp. 1-6 (2014).

(Continued)

*Primary Examiner* — John Pak
*Assistant Examiner* — Nathan W Schlientz
(74) *Attorney, Agent, or Firm* — Fay Sharpe LLP

(57) ABSTRACT

Extract of a bacterial strain for its use in treatment and/or care of the skin and/or mucous membranes, as well as its cosmetic and/or dermopharmaceutical compositions. In particular, its use for sebum reduction and skin firmness.

19 Claims, 1 Drawing Sheet

(56) References Cited

OTHER PUBLICATIONS

Nevot, et al., "Characterization of outer membrane cesicles released by the psychrotolerant bacterium Pseudoalteromonas Antarctica NF3," Environmental Microbiology, vol. 8, No. 9, pp. 1523-1533 (2006).
Kalinovskaya, et al., "Low-molecular-weight, biologically active compounds from marine Pseudoalteromonas species," Current Microbiology, vol. 48, No. 6, pp. 441-446 (2004).
Nieman, et al., "Development and Homeostasis of the sebaceous gland", Seminars in Cell & Developmental Biology vol. 23, pp. 928-936 (2012).
Bednarek, et al, "Potent and Selective Peptide Agonists of α-Melanocyte Stimulating Hormone (αMSH) Action at Human Melanocortin Receptor 5; their Synthesis and Biological Evaluation in vitro", Chem. Biol. Drug. Des., vol. 69, pp. 350-355 (2007).
Soap, Perfumery & Cosmetics (SPC), Product Innovation, pp. 4-6 (Apr. 2013).

\* cited by examiner

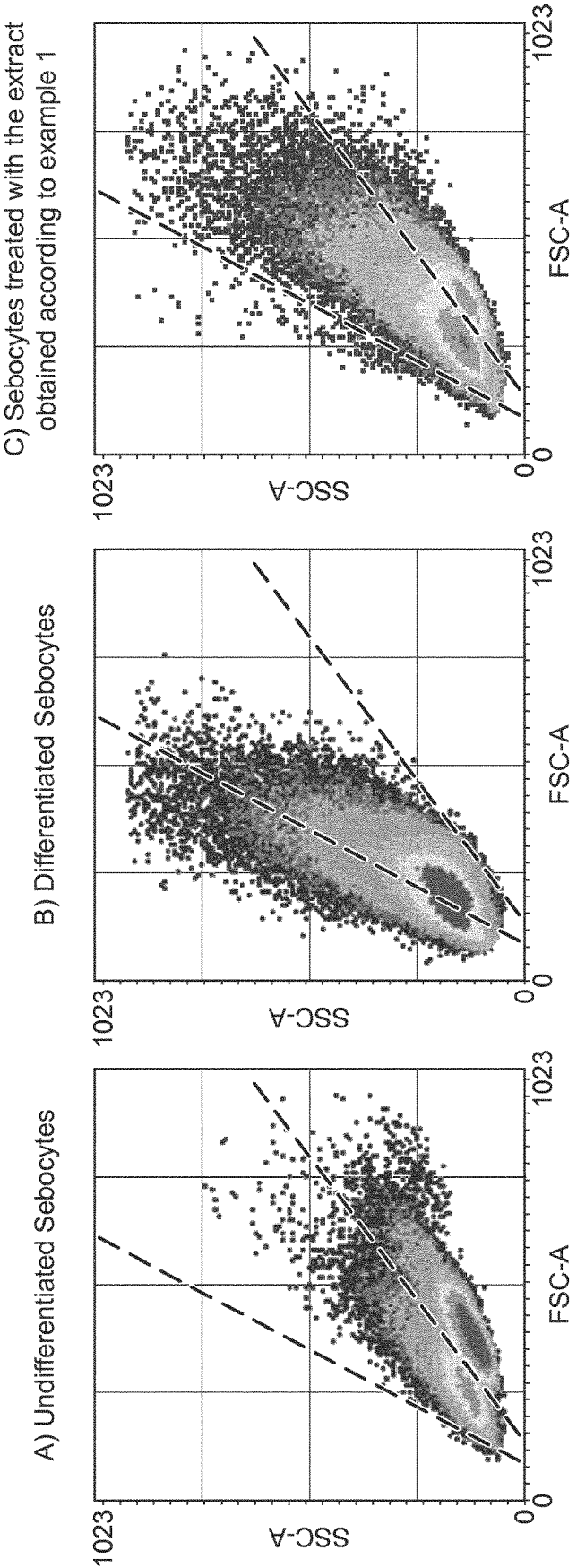

COSMETIC AND/OR PHARMACEUTICAL COMPOSITION CONTAINING A BACTERIAL EXTRACELLULAR PRODUCT FROM PSEUDOALTEROMONAS ANTARCTICA, AND USE THEREOF

This application claims the priority of PCT Appln. No. PCT/EP2015/075485 filed Nov. 2, 2015 which claims priority to European application no. 14382430.8 filed Oct. 31, 2014 the disclosures of which are incorporated in their entireties by reference herein.

FIELD OF THE INVENTION

This invention relates to an extracellular product of bacterial origin, which promotes sebum reduction. Said product is secreted by a strain of the *Pseudoalteromonas antarctica* species. This invention also relates to the use of said extracellular product of bacterial origin in cosmetic or dermopharmaceutical compositions for the treatment and/or care of the skin, mucous membranes and/or hair.

BACKGROUND OF THE INVENTION

The skin, mucous membranes, hair and/or nails constitute a physical barrier between the organism and its environment. The skin is composed of two tissues: the epidermis and the dermis. The epidermis is the outermost layer of the skin which is impermeable and therefore provides protection from external agents. It is a keratinized pluristratified epithelium which is continually renewing itself.

The epidermis has a high content in keratin, coming from the main type of cells in the epidermis (keratinocytes), melanin, and a significant content of lipids, which are found either in the stratum corneum or in the hydrolipidic film in the cutaneous surface. Lipids of sebaceous and keratinocyte origin are found in the lipidic film which covers the cutaneous surface, where the main part of these lipids are of sebaceous origin [A. Pappas, "*Epidermal Surface Lipids*", *Dermato-Endocrinology* 2009, 1, 72-76].

The sebaceous secretion is produced in the sebaceous glands, which are found all over the body, but the hands and feet palms, and they are found at densities of 400-900 glands per cm$^2$ in the face [K. R. Smith and D. M. Thiboutot, "*Sebaceous gland lipids: friend or foe?*", *Journal of Lipid Research* 2008, 49, 271-281], mainly associated to the hair follicle, where the sebaceous secretions arrive to the skin surface through its channel. The secretion of the sebaceous glands, the sebum, is an oily and waxy substance consisting of a mixture mainly constituted by fatty acids, diglycerides, triglycerides, cholesterol and squalene, which provides thermoregulating functions and decrease of water loss from the skin surface.

In human beings, the amount of produced sebum ranges according to the population group, depending on the age and hormonal factors of regulation, too. Depending on the amount of sebum, it is distinguished among:

Oily skin. Oily skin is caused by an excessive function of the sebaceous glands. When there is an excess of sebum in the skin, the skin is characterized by a thicker texture, a greasy and brilliant appearance, as well as by the presence of expanded pores and cutaneous imperfections.

Combination skin. It is characterized by the simultaneous presence of dry and oily areas. Commonly, the oily area is located on the forehead, nose and chin (known as T-zone). The part of the face outside of the T-zone is normally the dry area, due to the thinner skin in this area, which increases its desquamation.

Dry skin. The lack of sebum implies a disability to retain enough hydration, which renders in a fragile skin with a higher tendency to desquamation and fine wrinkles. With the characteristic of showing imperceptible pores, the reduced capacity of barrier function implies a higher susceptibility to harmful external factors such as UV, cold and wind.

Normal skin. With an appropriate amount of sebum which allows a good hydric balance, this kind of skin shows a good elasticity and resistance, with almost no visible pores and uniform skin tone.

Although dependent to a great extent on age and ethnic origin, there is an important average of population showing oily skin, together with the additional existence of the population with combination skin with an oily T-zone.

Some dermatological disorders related with excess sebum are:

Seborrhea, a functional disorder of the sebaceous glands which produce a hypersecretion of sebum, which causes red, irritated and squamous skin.

Acne, an infection which occurs when there is a stopping in the pores of the skin where sebum, dead cells and bacteria are entrapped.

Comedo, an accumulation of hardened sebum and a mass of keratinized cells which cause a blockage of the way in to the follicle.

Milium or milk spots, an accumulation of keratinized cells and sebaceous material entrapped under the skin.

Inside the sebaceous glands, sebum is released when the mature sebocytes rupture inside of the gland, and sebum goes out to the skin surface through the channel of the hair follicle. Until arriving to the sebum release, the gland function understands that there is a population of non-differentiated cells in the adjacent layer to the hair follicle which start their proliferation as they move to the basal layer of the gland, and they turn into lipid-filled sebocytes as they arrive to the central part of the gland, where they eventually and progressively break out [C. Nieman and V. Horsley, "*Development and Homeostasis of the sebaceous gland*", *Seminars in Cell & Developmental Biology* 2012, 23, 928-936].

A large number of compounds has shown their effects in regulating the function of sebaceous glands such as androgens, estrogens, retinoids, LXR type receptors (liver X receptor), receptors activated by peroxisome proliferators, growth hormones/insulin-like growth factors, and the family of melanocortins [K. R. Smith and D. M. Thiboutot, "*Sebaceous gland lipids: friend or foe?*", *Journal of Lipid Research* 2008, 49, 271-281].

The family of melanocortins is composed by a group of peptides structurally related with propiomelanocortin (POMC), and with the melanocortin receptors (MCRs) which regulate the effects of the melanocortinic peptides. MCRs are associated to G proteins (GPCRs) and transfer the signalling by different pathways: production of cyclic adenosine monophosphate (cAMP), activation of the protein kinase A, and increase of the concentration of [Ca$^{2+}$] cation.

MC5R is one of the different melanocortin receptors that have been characterized in various human tissues, and it is involved in lipid production [M. A. Bednarek et al, "*Potent and Selective Peptide Agonists of α-Melanocyte Stimulating Hormone (αMSH) Action at Human Melanocortin Receptor 5; their Synthesis and Biological Evaluation in vitro*", *Chem. Biol. Drug. Des.* 2007, 69, 350-355]. For example, transgenic mice that lacked expression of MC5R receptor showed a marked reduction in sebum production [D. M. Thibotout et al, *"The Melanocortin 5 Receptor is Expressed in Human Sebaceous Glands and Rat Preputial Cells"*, J. Invest. Dermatol. 2000, 115, 614-619]. Furthermore, MC5R is considered a marker of sebocyte differentiation since MC5R is not detected in undifferentiated sebaceous cells while it is detected in sebaceous cells in the later stages of differentiation, but not in basal, undifferentiated sebaceous cells. Similarly, MC5R is only detectable in in-vitro cultures at the onset of differentiation and in fully differentiated sebaceous cells showing prominent lipid granules [L. Zhang et al, *"Melanocortin-5 receptor: A marker of human sebocyte differentiation"*, Peptides 2006, 27, 413-420]. Since MC5R is a marker that correlates with the sebaceous differentiation process that leads to the production of sebum, the inhibition of this receptor MC5R may be used as a strategy for the reduction of sebum production and consequently for the treatment and/or prevention of disorders and/or diseases related with excess of sebum.

Furthermore the inhibition of MC5R receptor has been shown to be beneficial in the treatment of seborrheic dermatitis, cancer and inflammatory diseases (US 2009/221558). For example, the Muir-Torre syndrome consists of adenomas in sebaceous glands associated with an internal adenocarcinoma (usually in colon, prostate, breast or ovary) and the prevention of sebaceous cell differentiation through the inhibition of the MC5R receptor can be effective in the treatment of tumor growth (US 2009/221558). It has also been seen that the inhibition of receptor MC5R is beneficial for the treatment of anorexia or cachexia (US 2003/110518) and for treating hidradenitis suppurativa and excessive production of cerumen (WO 03/040118 A1).

It is also known that certain compounds, such as estrogens, which inhibit sebaceous glands have a stimulatory effect on collagen synthesis, and therefore have a skin firming effect [A. Parchami, R. A. Fatahian Dehkordi, *"Effect of ovariectomy and chronic sex steroid administration on rabbit skin"*, Global Veterinaria, 2010, 4(6), 610-615].

It is described in the prior art an extracellular polymeric substance coming from the sea, Matmarine™, which acts on MC5R receptor [*Soap, Perfumery & Cosmetics, Product Innovation* 2013, page 39]. Matmarine™ is said to decrease the sebum rate (8.4%), number (20.5%) and area of pores (18.8%).

Surprisingly, the applicant of the present invention has found that extracts of molecular weight below 10 kDa produced by strains of *Pseudoalteromonas antarctica* inhibit the MC5R receptor and increase collagen synthesis in the skin.

It is known from the prior art that a glycoprotein produced by the species *Pseudoalteromonas antarctica* has properties of healing (EP 1402898 B1), moisturizing and it repairs skin keratinization disorders (EP 2337556 A1). The prior art also discloses a profile of proteins at the membrane vesicle of *Pseudoalteromonas antarctica* with molecular weights of 109 KDa, 52.5 KDa, 48 KDa, 44 KDa, 42 KDa, 34.5 KDa, 33 KDa, 31 KDa and 24 KDa. The average molecular weight of the main protein is between 98 and 112 KDa [Morphological and physiological study of *Pseudoalteromonas antarctica* NF3 and characterization of membrane vesicles present in the produced extracellular material, Doctoral Thesis of Maria Nevot, filed at the University of Barcelona].

SUMMARY OF THE INVENTION

The disclosed technology provides a solution for the reduction of serum in the skin, mucous membranes and/or hair by an extract of a strain of *Pseudoalteromonas antarctica* species.

In accordance with one aspect of the invention, a method of treatment and/or care of the skin mucous membranes and/or hair of a subject includes administering a cosmetically or dermopharmaceutically effective quantity of an extract of molecular weight under 10,000 Da produced by a strain of *Pseudoalteromonas antarctica* species to the skin, mucous membranes and/or hair of the subject.

In accordance with another aspect of the invention, a cosmetic or dermopharmaceutical composition includes a cosmetically or dermopharmaceutically effective quantity cosmetically or dermopharmaceutically effective quantity of an extract of molecular weight under 10,000 Da produced by a strain of *Pseudoalteromonas antarctica* species and at least one cosmetically and/or dermopharmaceutically acceptable excipient, adjuvant and/or ingredient.

BRIEF DESCRIPTION OF THE DRAWING

FIG. 1: Density plots show morphological parameters of size (FSC-A) and granularity (SSC-A) for sebocytes grown in different culture conditions. Undifferentiated sebocytes show two main cell populations with similar granularity levels but two different sizes. Differentiated sebocytes show a unique cell population characterized by high granularity levels and small cell size. Sebocytes treated with 2.5 µg/ml of the extract obtained according to example 1, show a change in morphology decreasing granularity and increasing cell size similar to undifferentiated sebocytes.

DESCRIPTION OF THE INVENTION

This invention relates to the cosmetic and/or dermopharmaceutical use of the extracts of molecular weight under 10,000 Da produced by *Pseudoalteromonas antarctica* species. Surprisingly, the inventors of this invention have found that the aforementioned extracts reduce the amount of sebum in the skin and/or hair, increase collagen synthesis in the skin, and they are photoprotectors, too. In one embodiment, the inhibition of the MC5R receptor reduces the sebum production in the skin and/or hair and it diminishes the amount of sebum.

Definitions

In order to facilitate the comprehension of this invention, the meanings of some terms and expressions as used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with this disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin, hair and/or mucous membranes in particular with the aim of improving the cosmetic qualities of the skin, hair and/or mucous membranes such as and not restricted to, their level of hydration, elasticity, firmness, shine, tone or texture, among others. The term "care" in this invention refers to the maintenance of the qualities of the skin, hair and/or mucous membranes. These qualities are subject to improvement and maintained through a cosmetic treatment and/or care of the skin, hair and/or mucous membranes both in healthy subjects as well as those which present diseases and/or disorders of the skin and/or mucous membranes, such as and not restricted to, ulcers and lesions on the skin, psoriasis, dermatitis, acne or rosacea, among others.

The term "prevention", as used in this invention, refers to the ability of a compound of the invention to prevent, delay or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, such as and not restricted to, flaccidity, sagging, changes to the color or irregularities in the pigmentation, abnormal and/or excessive keratinization.

Therefore, a first aspect of the present invention relates to the extract of molecular weight under 10,000 Da produced by a strain of *Pseudoalteromonas antarctica* species for its use in the treatment of the skin and/or mucous membranes. In one embodiment, the treatment refers to the treatment and/or prevention of inflammation, skin cancer, comedones, milia, acne, seborrhea, seborrheic dermatitis, hidradenitis suppurativa or photoprotection of the skin. In one embodiment, the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, inflammation of the mucous membrane of the vagina, inflammation of the oral mucous membrane, gingivitis, periodontitis, rhinitis, allergic rhinitis, among others.

In another embodiment, the present invention relates to the extract of molecular weight under 10,000 Da produced by a strain of *Pseudoalteromonas antarctica* species for its use in the treatment of cancer, anorexia or cachexia. In one embodiment, the treatment of cancer is a treatment of inhibition of the tumor growth or to the Muir-Torre syndrome.

In another aspect, the present invention relates to the use of the extract of molecular weight under 10,000 Da produced by a strain of *Pseudoalteromonas antarctica* species for the cosmetic, non-therapeutic treatment and/or care of the skin, mucous membranes and/or hair. In one embodiment, the cosmetic, non-therapeutic treatment and/or care of the skin, mucous membranes and/or hair is a treatment of reduction of the sebum amount in the skin and/or hair, treatment and/or prevention of skin aging, treatment and/or prevention of skin wrinkles, treatment of skin firming, prevention of loss of skin firmness, and/or hair hygiene.

In another embodiment, the treatment of the skin and/or mucous membranes, and the cosmetic, non-therapeutic treatment and/or care of the skin, mucous membranes and/or hair inhibit the MC5R receptor.

In another embodiment, the treatment of the skin and/or mucous membranes, and the cosmetic, non-therapeutic treatment and/or care of the skin, mucous membranes and/or hair stimulate collagen synthesis.

In another embodiment, the treatment of the skin and/or mucous membranes, and the cosmetic, non-therapeutic treatment and/or care of the skin, mucous membranes and/or hair is carried out by topical or transdermal application.

In another embodiment, the molecular weight of the extract produced by a strain of *Pseudoalteromonas antarctica* species is higher than 50 Da and lower than 10,000 Da, is between 100 Da and 8,000 Da, between 150 Da and 6,000 Da, or between 300 Da and 5,000 Da.

In another embodiment, the strain of *Pseudoalteromonas antarctica* species is the strain with deposit number CECT 8690. Said strain has been deposited on Jul. 29, 2014 at the Colección Española de Cultivos Tipo (CECT) (Edificio 3 CUE, Parc Cientific Universitat de Valencia, Catedrático Agustín Escardino 9, 46980 Paterna, Valencia, Spain) as institution legally recognized for said purpose according to the Budapest Treaty on the International Recognition of the Deposit of Microorganisms on Apr. 28, 1977.

In another embodiment, the extract of molecular weight under 10,000 Da can be obtained through fermentation of a strain of *Pseudoalteromonas antarctica* species in a suitable culture medium, conventionally stirred and aerated for synthesizing and secreting said product to the culture medium followed by the isolation and purification. Fermentation to produce the extract of this invention can be carried out in a medium stirred and aerated at a temperature between 5° C. and 37° C., or between 8° C. and 20° C., the medium having a pH between 5.5 and 9, or between 6.5 and 7.5, adjusting it if necessary during fermentation. The duration of the fermentation is between 24 to 120 hours, or between 36 and 72 hours. In one embodiment, the method of isolation and purification of the extract of molecular weight under 10,000 Da is carried out by the methods known by the person skilled in the art such as, centrifugation and filtration. After the centrifugation and filtration steps directed to separate the strain of the *Pseudoalteromonas antarctica* species from the supernatant where the extract is found, filtrations to eliminate molecules of high molecular weight are done in order to purify this extract and membranes which retain molecules of a molecular weight greater than 10,000 Da are used. In one embodiment, the strain of *Pseudoalteromonas antarctica* species is the strain with deposit number CECT 8690.

In another embodiment, the extract of molecular weight under 10,000 Da of the strain of *Pseudoalteromonas antarctica* species has a retention time between 5 and 20 minutes, or between 8 and 17 minutes at a chromatographic analysis High Performance Liquid Chromatography (HPLC), with a chromatographic column TSKGel G2000SWXL, 5 m, 125 Å 7.8 mm×30 mm (TOSOH Bioscience) and water with 0.1M pH=6.70+0.1M phosphate buffer+0.1M sodium sulfate as eluent.

In one embodiment, in the fermentation of the strain of *Pseudoalteromonas antarctica* species some exogenous sugars, such as and not restricted to, galactose, glucose, mannose, amygdalin, cellobiose, maltose, starch, glycogen, lactose, mixtures thereof and/or extracts containing mixtures of these sugars can be used as a source of carbon. In one embodiment, an exogenous supply of glucose of 2 to 40 g/L, or 10 to 30 g/L, is provided.

In another embodiment, the culture medium comprises additional nitrogen or carbon sources such as yeasts extracts, malt extracts or peptones, with concentrations of each one of these components from 0.1 to 20 g/L, or from 0.5 to 10 g/L.

In another embodiment, mineral salts are also provided for the fermentation culture of the strain of *Pseudoalteromonas antarctica* species and the mineral salts are selected from among salts which provide the ions $Na^+$, $K^+$, $NH_4^+$, $Ca^{2+}$, $Mg^{2+}$, $PO_4^{3-}$, $SO_4^{2-}$, $Cl^-$, $CO_3^{2-}$, or trace elements such as Cu, Mn, Fe and Zn.

Another aspect of this invention relates to a cosmetic or dermopharmaceutical composition characterized in that it comprises a cosmetically or dermopharmaceutically effective quantity of the extract of molecular weight under 10,000 Da produced by a strain of *Pseudoalteromonas antarctica* species and at least one cosmetically and/or dermopharmaceutically acceptable excipient, adjuvant and/or ingredient. Said compositions can be prepared by the conventional methods known by the persons skilled in the art [*"Harry's Cosmeticology"*, Seventh edition, (1982), Wilkinson J. B., Moore R. J., ed. Longman House, Essex, GB]. In one embodiment, the strain of *Pseudoalteromonas antarctica* species is the strain with deposit number CECT 8690.

The cosmetically or dermopharmaceutically effective quantity of the extract of molecular weight under 10,000 Da produced by a strain of *Pseudoalteromonas antarctica* species in the composition of the invention to be administered, as well as its dosage, will depend on numerous factors, including age, condition of the patient, the nature or severity of the condition, disorder or disease to be treated and/or cared for, the route and frequency of administration of the extract.

"Cosmetically or dermopharmaceutically effective quantity" is understood to be a non-toxic but sufficient quantity of the extract of molecular weight under 10,000 Da produced by a strain of *Pseudoalteromonas antarctica* species to provide the desired effect. The extract of the invention is used at cosmetic or dermopharmaceutical concentrations to achieve the desired effect; in one embodiment, with regard to the total weight of the composition, between 0.0000000001% (in weight) and 20% (in weight); or between 0.00000001% (in weight) and 10% (in weight), or between 0.000001% (in weight) and 5% (in weight), or between 0.0001% (in weight) and 5% (in weight).

In another embodiment, the extract of the invention can also be incorporated into cosmetic and/or dermopharmaceutical delivery systems and/or sustained release systems.

The term "delivery systems" relates to a diluent, adjuvant, vehicle or additives with which the extract of the invention is administered. These cosmetic or pharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or additives which can be used in the different delivery systems in which the extract of the invention can be administered.

The term "sustained release" is used in a conventional sense relating to a delivery system of a compound which provides the gradual release of this compound during a period of time and in one embodiment, although not necessarily, with relatively constant compound release levels over a period of time.

Examples of delivery or sustained release systems include, without limiting sense, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as microemulsions and nanoemulsions, which can be added to achieve a greater penetration of the active ingredient of the invention and/or to improve the pharmacokinetic and pharmacodynamic properties of it. In one embodiment, the delivery or sustained release systems are liposomes, surfactant-phospholipid mixed micelles and microemulsions, and water-in-oil microemulsions with an internal reverse micelle structure and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part. In one embodiment, the sustained release system should release a relatively constant quantity of the extract of the invention. The amount of extract contained in the sustained release system will depend, for example, on where the composition is to be administered, the kinetics and duration of the release of the extract of the invention, as well as the nature of the condition, disorder and/or disease to be treated or prevented.

The composition containing the extract of this invention can also be adsorbed on solid organic polymers or solid mineral supports, such as and not restricted to, talc, bentonite, silica, starch or maltodextrin among others.

The compositions containing the extract of molecular weight under 10,000 Da produced by a strain of *Pseudoalteromonas antarctica* species can also be incorporated into fabrics, non-woven fabrics or medical devices which are in direct contact with the skin, thus releasing the extract of the invention whether by biodegradation of the binding system to the fabric, non-woven fabric or medical device, or due to the friction between them and the body, due to body moisture, the skin's pH or body temperature. Furthermore, the extract of the invention can be incorporated into the fabrics and non-woven fabrics used in the manufacture of garments that are in direct contact with the body. In one embodiment, the fabrics, non-woven fabrics and medical devices containing the extract of the invention are used for the treatment and/or prevention of conditions, disorders and/or diseases which improve or are prevented by the inhibition of MC5R receptor, or by stimulation of collagen synthesis.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) HAPPI May 1986; Nelson G., "Application of microencapsulation in textiles", (2002), Int. J. Pharm., 242(1-2), 55-62; "Biofunctional Textiles and the Skin" (2006) Curr. Probl. Dermatol. v. 33, Hipler U. C. and Elsner P., eds. S. Karger A G, Basel, Switzerland; Malcolm R. K. et al., "Controlled release of a model antibacterial drug from a novel self-lubricating silicone biomaterial," (2004), J. Cont. Release, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or dermopharmaceutical compositions containing the extract of this invention can be used in different types of compositions of topical or transdermal application, optionally including cosmetically and/or dermopharmaceutically acceptable excipients necessary for formulating the desired administration form.

The compositions of topical or transdermal application can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated, using techniques known by the person skilled in the art, into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic or dermopharmaceutical compositions of the invention may include agents which increase the percutaneous absorption of the compounds of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the extract of the invention. The application area will be determined by the nature of the condition, disorder and/or disease to be treated and/or prevented.

Among the cosmetically or dermopharmaceutically acceptable excipients, adjuvants and/or ingredients contained in the cosmetic or dermopharmaceutical compositions described in this invention are additional ingredients commonly used in cosmetic or dermopharmaceutical compositions such as and not restricted to, other agents which diminish the sebum production, anti-seborrheic agents, mattifying agents, anti-acne agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, other anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of lipids and components of the stratum corneum, ceramides, fatty acids, agents that inhibit collagen degradation, agents that inhibit matrix metalloproteinases, agents that inhibit elastin degradation, agents that inhibit serine proteases such as kallikreins, leukocyte elastase or cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, binding agents, lipolytic agents or agents stimulating lipolysis, adipogenic agents, agents modulating PGC-1α expression, agents modulating the activity of PPARγ, agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents which improve dermal-epidermal junction, agents inducing hair growth, hair growth inhibiting or retardant agents, hair loss retardant agents, preservatives, perfumes, odor absorbents and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and particularly with the extract of molecular weight under 10,000 Da produced by the strain of *Pseudoalteromonas antarctica* species. Likewise, the nature of these additional ingredients should not unacceptably alter the benefits of the extract of this invention. The nature of these additional ingredients can be synthetic or natural, such as plant extracts, or come from a biotechnological process, or from a combination of a synthetic process and a biotechnological process. Additional examples can be found in *CTFA International Cosmetic Ingredient Dictionary & Handbook,* 12*th Edition* (2008). In the context of this invention, biotechnological process is understood to be any process to produce the active ingredient, or part of it, in an organism, or in part of it.

In one embodiment, the cosmetic and/or dermopharmaceutical composition of the invention contains:
  between 0.0000000001% (in weight) and 20% (in weight) of the extract of molecular weight under 10,000 Da produced by a strain of *Pseudoalteromonas antarctica* species;
  between 0.1% (in weight) and 20% (in weight) of an humectant selected from the group of (INCI Names) Glycerin, Propylene Glycol, Butylene Glycol, Pentylene Glycol, Caprylyl Glycol, Lactic Acid, Urea, Sodium Hyaluronate;
  between 0.1% (in weight) and 20% (in weight) of an emollient or skin conditioning selected from the group of (INCI Names) Dimethicone, Glyceryl Stearate, Caprylic/Capric Triglyceride, Cetearyl Alcohol, Lecithin, C12-15 Alkyl Benzoate, Squalane, Lanolin, Behenyl Alcohol, Tocopheryl Acetate, Panthenol, *Butyrospermum Parkii* Butter, Retinyl Palmitate, Retinol;
  between 0.1% (in weight) and 20% (in weight) of a surfactant selected from the group of (INCI Names) Xanthan Gum, Sodium Laureth Sulfate, Stearic Acid, Polysorbate 20, Polysorbate 80, Stearyl Alcohol, Cetyl Alcohol, Steareth-2, Ceteareth-20, Cocamidopropyl Betaine.

In one embodiment, the agent which diminishes the sebum production, anti-seborrheic agent, mattifying agent, anti-acne agent is selected, for example and not restricted to, from the group formed by Mat-XS™ Clinical [INCI: Sarcosine, Xanthan gum], Mat-XS™ Bright [INCI: *Orthosiphon Stamineus* Leaf Extract, Maltodextrin, Xanthan Gum], Betapur™ [INCI: Peumus Boldus Leaf Extract, Xanthan Gum] or Neurobiox™ [INCI: *Achillea Millefolium* Extract, Xanthan Gum] marketed by BASF, Evermat™ [INCI: *Enantia Chlorantha* Bark Extract, Oleanolic Acid], Ac.net™ [INCI: Butylene Glycol, Peg-60 Almond Glycerides, Caprylyl Glycol, Glycerin, Carbomer, Nordihydroguaiaretic Acid, Oleanolic Acid] or Sebuless™ [INCI: Maltodextrin, *Syringa Vulgaris* (Lilac) Extract] marketed by Sederma/Croda, Phytessence™ Purple *Ginseng* [INCI: Glycerin or *Polygonum Bistorta* Root Extract] marketed by Crodarom, P-Refinyl® [INCI: *Lens Esculenta* (Lentil) Seed Extract], marketed by Silab, EPS Seamat™ [INCI: Planktonic Exopolysaccharide-5, Phenoxyethanol] or Epidermist™ 4.0 [INCI: Plankton Extract], marketed by Codif, Seborami™ [INCI: *Sisymbrium Officinale* Extract, *Arctium Lappa* Root Extract, Citric Acid, Glycolic Acid, Zinc PCA, *Sclerotium* Gum] marketed by Alban Muller, Poreaway™ [INCI: *Pistacia Lentiscus* Gum/*Pistacia Lentiscus* (Mastic) Gum, Lecithin] marketed by Mibelle, Citrustem™ [INCI: Xanthan Gum, Sodium Benzoate, Gluconolactone, Calcium Gluconate] or Affipore™ [INCI: *Barosma Betulina* Leaf Extract, Citric Acid], marketed by Provital, Sweetone® [INCI: Saccharide Hydrolysate, Maltodextrin], marketed by Laboratoires Expanscience, Seboxyl® [INCI: *Ribes Nigrum* (Black Currant) Leaf Extract, *Rubus Idaeus* (Raspberry) Leaf Extract] or Saniskin® [INCI: *Polygonum Cuspidatum* Root Extract, Myristyl Alcohol], marketed by Solabia, Alpaflor® Alp®-Sebum [INCI: *Epilobium Fleischeri* Extract, Citric Acid, Potassium Sorbate] or Regu®-Seb [INCI: *Argania Spinosa* Kernel Extract, *Serenoa Serrulata* Fruit Extract, *Sesamum Indicum* (Sesame) Seed Extract], marketed by DSM, Dermaclarine™ [INCI: Hydrolyzed Egg Protein (and) Protease] marketed by Aqua Bio Technology, Linumine™ [INCI: *Linum Usitatissimum* (Linseed) Seed Extract], marketed by Lucas Meyer, Granactive Acne™ [INCI: *Oryza Sativa* (Rice) Bran Extract, *Boswellia Serrata* Extract, Honey Extract, Oligopeptide-10], marketed by Evonik, Sepicontrol™ A5 [INCI: Capryloyl Glycine, Sarcosine, *Cinnamonium Zeylanicum* Bark Extract], marketed by Seppic, Sympeptide® 380 [INCI: Myristoyl Hexapeptide-23] marketed by Symrise, or Sebaryl™ [INCI: Niacinamide, Yeast Extract, *Aesculus Hippocastanum* (Horse Chestnut) Seed Extract, Ammonium Glycyrrhizate, Panthenol, Propylene Glycol, Zinc Gluconate, Caffeine, Biotin], marketed by Laboratoires Serobiologiques/Cognis/BASF, among others.

In one embodiment, the anti-wrinkle and/or antiaging agent is selected, for example and not restricted to, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage™ [INCI: teprenone], Resistem™ [INCI: *Globularia Cordifolia* Ferment], Beautifeye™ [INCI: *Albizia Julibrissin* Bark Extract, Darutoside], Meiritage [INCI: *Astragalus Membranaceus* Root Extract, Atractyloides *Macrocephala* Root Extract, Bupleurum Falcatum Root Extract], Senestem [INCI: *Plantago Lanceolata* Leaf Extract], Venuceane™ [INCI: *Thermus Thermophillus* Ferment] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum], Regu-Scence™ [INCI: *Asparagus Officinalis* Stem Extract, Sodium Benzoate, Potassium Sorbate, Gluconolactone, Calcium Gluconate], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9], Shadownyl™ [INCI: Algae Extract, Hexylene Glycol, Caprylyl Glycol, Xanthan Gum] or DN AGE™ LS [INCI: *Cassia alata* leaf Extract] marketed by Laboratoires Sérobiologiques/Cognis/BASF, Algisum C® [INCI: Methylsilanol Mannuronate], Exage™ [INCI: Imidazolylethyl Diaminopropanamide] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Serilesine® [INCI: Hexapeptide-10], Leuphasyl® [INCI: Pentapeptide-18], Inyline® [INCI: Acetyl Hexapeptide-30], Aldenine® [INCI: Hydrolized Wheat Protein, Hydrolyzed Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide-10 Citrulline], Hyadisine® [INCI: *Pseudoalteromonas* Ferment Extract], Hyanify™ [INCI: Saccharide Isomerate], Diffuporine® [INCI: Acetyl Hexapeptide-37], Silusyne® [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline® [INCI: Acetyl Hexapeptide-38], Uplevity™ [INCI: Acetyl Tetrapeptide-2], Juveleven™ [INCI: Acetyl Hexapeptide-51 Amide] or Telangyn™ [INCI: Acetyl Tetrapeptide-40] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Peptide Q10™ [INCI: Pentapeptide-34 Trifluoroacetate], Telosense™ [INCI: Hydrolyzed Yeast Protein, Hydrolyzed Soy Protein] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium/Unipex Innovations, EquiStat [INCI: *Pyrus malus* Fruit Extract, *Glycine soja* Seed Extract] or Juvenesce™ [INCI: Ethoxydiglycol and Caprylic Triglyceride, Retinol, Ursolic Acid, Phytonadione, Ilomastat] marketed by Coletica/Engelhard/BASF, Ameliox™ [INCI: Carnosine, Tocopherol, *Silybum marianum* Fruit Extract], Phytocelltec™ Symphytum [INCI: Isomalt, *Symphytum Officinale* Root Cell Culture, Lecithin, Sodium Benzoate], Snow Algae Powder [INCI: Chlamydocapsa Extract, Maltodextrin, Lecithin], Dermcom™ [INCI: Acacia Senegal Gum, *Crocus Chrysanthus* Bulb Extract], Anagain™ [INCI: *Pisum Sativum* (Pea), Sprout Extract] or PhytoCellTec™ *Malus Domestica* [INCI: *Malus domestica* Fruit Cell Culture] marketed by Mibelle Biochemistry, Bioxilift® [INCI: *Pimpinella anisum* Extract], Vitagenyl® [INCI: *Prunus Persica* (Peach) Leaf Extract] or SMS Anti-Wrinkle® [INCI: *Annona squamosa* Seed Extract] marketed by Silab, Symvital® Agerepair [INCI: *Zingiber Off icinale* (Ginger) Root Extract] marketed by Symrise, Citrustem™ [INCI: Xanthan Gum, Sodium Benzoate, Gluconolactone, Calcium Gluconate], Melavoid™ [INCI: *Boerhavia Diffusa* Root Extract], Darkout™ [INCI: *Hypoxis Rooperi* Rhizome Extract, *Caesalpinia Spinosa* Gum] or Linefill™ [INCI: Dimethyl Isosorbide, *Sesamum Indicum* (Sesame) Seed Extract] marketed by Provital, Adipofill'in™ [INCI: Ornithine, Phospholipids, Glycolipids], Elix-IR™ [INCI: *Polygonum Aviculare* Extract] or Progeline™ [INCI: Trifluoroacetyl Tripeptide-2] marketed by Lucas Meyer, Amiperfect™ [INCI: *Gaultheria Procumbens* (Wintergreen) Leaf Extract] or Repulpami™ ER [INCI: *Adansonia Digitata* Pulp Extract, *Hibiscus Sabdariffa* Flower Extract] marketed by Alban Muller, Celloxyl® [INCI: *Uapaca Bojeri* Leaf Extract] or Resistress® [INCI: *Sophora Japonica* Flower Extract] marketed by Solabia, Actiporine™ 8G [INCI: *Jania Rubens* Extract] or EPS Seafill™ [INCI: Plankton Extract] marketed by Codif, Novhyal® Biotech G [INCI: Disodium Acetyl Glucosamine Phosphate] or Rubixyl® [INCI: Hexapeptide-47] marketed by Induchem, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

In another embodiment, the anti-inflammatory agent and/or analgesic is selected, for example and not restricted to, from the group formed by extract of madecassoside, extract of *echinacea*, amaranth seed oil, sandal wood oil, extract of peach tree leaf, extract of *Aloe vera*, *Arnica montana*, *Artemisia vulgaris*, *Asarum maximum*, *Calendula officinalis*, *Capsicum*, *Centipeda cunninghamii*, *Chamomilla recutita*, *Crinum asiaticum*, *Hamamelis virginiana*, *Harpagophytum procumbens*, *Hypericum perforatum*, *Lilium candidum*, *Malva sylvestris*, *Melaleuca alternifolia*, *Origanum majorana*, *Origanum vulgare*, *Prunus laurocerasus*, *Rosmarinus officinalis*, *Salix alba*, *Silybum marianum*, *Tanacetum parthenium*, *Thymus vulgaris*, *Uncaria guianensis* or *Vaccinium myrtillus*, omega-3 and omega-6 fatty acids, Neutrazen™ [INCI: Water, Butylene Glycol, Dextran, Palmitoyl Tripeptide-8] marketed by Atrium Innovations/Unipex Group, Delisens™ [proposed INCI: Acetyl Hexapeptide-46] marketed by Lipotec/Lubrizol, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis/BASF, Calmosensine™ [INCI: Acetyl Dipeptide-1] marketed by Sederma/Croda, coenzyme Q10 or alkyl glyceryl ethers.

In another embodiment, the firming and/or redensifying and/or restructuring agent is selected, for example and not restricted to, from the group formed by extracts of *Malpighia punicifolia, Cynara scolymus, Gossypium herbaceum, Aloe Barbadensis, Panicum miliaceum, Morus nigra, Sesamum indicum, Glycine soja, Triticum vulgare,* Pronalen® Refirming HSC [INCI: *Triticum Vulgare, Silybum Marianum,* Glycine Soy, *Equisetum Arvense, Alchemilla Vulgaris, Medicago Sativa, Raphanus Sativus*], Lipoout [INCI: Plankton Extract] or Polyplant® Refirming [INCI: Coneflower, *Asiatic Centella,* Fucus, Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, Aractostaphylos Uva Ursi Leaf Extract], Cytokinol® LS [INCI: Hydrolyzed Casein, Hydrolyzed Yeast Protein, Lysine HCl] or Firmiderm® LS9120 [INCI: *Terminalia Catappa* Leaf Extract, *Sambucus Nigra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate], Eperuline™ [INCI: Maltodextrin, *Eperua Falcata* Bark Extract] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, *Sclerotium* Gum] marketed by Atrium Biotechnologies/Unipex Innovations, Sphingokine® NP [INCI: Caprooyl Phytosphingosine] marketed by Evonik, Body3 Complex™ [INCI: Bentonite, *Butyrospermum Parkii* (Shea) Nut Extract, *Persea Gratissima* (Avocado) Fruit Extract] marketed by Lucas Meyer, ProSynergen™ DF [INCI: *Lactobacillus/Ulkenia* Amoeboidea Ferment Extract Filtrate] marketed by Lonza or IP2000™ [INCI: Dextran, Trifluoroacetyl Tripeptide-2] marketed by Institut Europeen de Biologie Cellulaire/Unipex Innovations, among others.

In another embodiment, the agent stimulating the synthesis of dermal or epidermal macromolecules is selected, for example and not restricted to, from the group formed by collagen synthesis-stimulating agents, elastin synthesis-stimulation agents, decorin synthesis-stimulation agents, laminin synthesis-stimulation agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, agents stimulating adipocyte proliferation, agents that accelerate or delay adipocyte differentiation, and DNA repairing agents and/or DNA protecting agents, such as and not restricted to extracts of *Centella asiatica, Saccharomyces cerevisiae, Solanum tuberosum, Rosmarinus officinalis, Vaccinium angustifolium,* extract of the algae *Macrocystis pyrifera, Padina pavonica,* extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of saline zooplankton, the fermentation product of milk with *Lactobacillus Bulgaricus,* asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: *Pseudoalteromonas* Ferment Extract], Decorinyl® [INCI: Tripeptide-10 Citrulline], Serilesine® [INCI: Hexapeptide-10], Lipeptide [INCI: Hydrolyzed Vegetable Protein], Aldenine® [INCI: Hydrolyzed Wheat Protein, Hydrolyzed Soy Protein, Tripeptide-1], Relistase™ [INCI: Acetylarginyltriptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Drieline® PF [INCI: Yeast Betaglucan] marketed by Alban Muller, Phytovityl C.® [INCI: Aqua, *Zea Mays* Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

Applications

In another aspect, this invention refers to the use of the extract of molecular weight under 10,000 Da produced by a strain of *Pseudoalteromonas antarctica* species in the preparation of a cosmetic or dermopharmaceutical composition for the treatment and/or care of the skin, mucous membranes and/or hair. In one embodiment, the treatment and/or care of the skin, mucous membranes and/or hair refers to the treatment and/or prevention of inflammation, cancer, comedones, milia, acne, seborrhea, seborrheic dermatitis, hidradenitis suppurativa, photoprotection of the skin, treatment of reduction of the sebum amount in the skin and/or hair, treatment and/or prevention of skin aging, treatment and/or prevention of skin wrinkles, treatment of skin firming, prevention of loss of skin firmness and/or hair hygiene. In one embodiment, the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, inflammation of the mucous membrane of the vagina, inflammation of the oral mucous membrane, gingivitis, periodontitis, rhinitis, allergic rhinitis, among others.

In another aspect, the present invention relates to the use of the extract of molecular weight under 10,000 Da produced by a strain of *Pseudoalteromonas antarctica* species in the preparation of a pharmaceutical composition for the treatment of cancer, anorexia or cachexia. In one embodiment, the treatment of cancer is a treatment of skin cancer, treatment of inhibition of the tumour growth or to the Muir-Torre syndrome.

In another aspect, this invention refers to the use of the extract of molecular weight under 10,000 Da produced by a strain of *Pseudoalteromonas antarctica* species in the preparation of a cosmetic or dermopharmaceutical composition for the inhibition of MC5R receptor.

In another aspect, this invention refers to the use of the extract of molecular weight under 10,000 Da produced by a strain of *Pseudoalteromonas antarctica* species in the preparation of a cosmetic or dermopharmaceutical composition for the stimulation of collagen synthesis.

An additional aspect of this invention refers to a method of treatment and/or care of the skin, mucous membranes and/or hair which comprises the administration of a cosmetically and/or dermopharmaceutically effective quantity of the extract of molecular weight under 10,000 Da produced by a strain of *Pseudoalteromonas antarctica* species. In one embodiment, the treatment and/or care of the skin, mucous membranes and/or hair refers to the treatment and/or prevention of inflammation, cancer, comedones, milia, acne, seborrhea, seborrheic dermatitis, hidradenitis suppurativa, photoprotection of the skin, treatment of reduction of the sebum amount in the skin and/or hair, treatment and/or prevention of skin aging, treatment and/or prevention of skin wrinkles, treatment of skin firming, prevention of loss of skin firmness and/or hair hygiene. In one embodiment the inflammation is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, inflammation of the mucous membrane of the vagina, inflammation of the oral mucous membrane, gingivitis, periodontitis, rhinitis, allergic rhinitis, among others.

In another aspect, the invention relates to a method of treatment of cancer, anorexia or cachexia which comprises the administration of a cosmetically and/or dermopharmaceutically effective quantity of the extract of molecular weight under 10,000 Da produced by a strain of *Pseudoalteromonas antarctica* species. In one embodiment, the treatment of cancer is a treatment of skin cancer, treatment of inhibition of the tumor growth or to the Muir-Torre syndrome.

In another aspect, this invention refers to a method of inhibition of MC5R receptor which comprises the administration of a cosmetically and/or dermopharmaceutically effective quantity of the extract of molecular weight under 10,000 Da produced by a strain of *Pseudoalteromonas antarctica* species.

In another aspect, this invention refers to a method of stimulation of collagen synthesis which comprises the administration of a cosmetically and/or dermopharmaceutically effective quantity of the extract of molecular weight under 10,000 Da produced by a strain of *Pseudoalteromonas antarctica* species.

In another embodiment, the molecular weight of the extract produced by a strain of *Pseudoalteromonas antarctica* species is higher than 50 Da and lower than 10,000 Da, is between 100 Da and 8,000 Da, between 150 Da and 6,000 Da, or between 300 Da and 5,000 Da.

In another embodiment, the strain of *Pseudoalteromonas antarctica* species is the strain with deposit number CECT 8690.

In another aspect, the extract of molecular weight under 10,000 Da produced by a strain of *Pseudoalteromonas antarctica* species can be administered by any means that causes its contact with the site of action in a mammal's body, preferably that of a human being, and in one embodiment in the form of a composition which contains it. The administration of the extract of molecular weight under 10,000 Da produced by a strain of *Pseudoalteromonas antarctica* species is carried out topically or transdermally. In one embodiment, topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of the application or administration can vary widely, depending on the needs of each subject, suggesting a range of application or administration from once per month to 10 times per day, from once per week to 4 times per day, from three times per week to three times per day, or once per day.

Deposit of Biological Material

The strain of the species *Pseudoalteromonas antarctica* species was deposited at the Colección Española de Cultivos Tipo (CECT) (Edificio 3 CUE, Parc Cientific Universitat de Valencia, Catedrático Agustin Escardino 9, 46980 Paterna, Valencia, Spain) under the conditions of the Budapest Treaty. The deposit was done on Jul. 29, 2014 and the deposit number was CECT 8690.

EXAMPLES

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as approximated, i.e., subject to a variability of ±5%, ±3%, ±1%, ±0.1%, or ±0.01% over the indicated value. It is to be understood that the upper and lower amount, range, and ratio limits set forth herein may be independently combined. Similarly, the ranges and amounts for each element of the technology described herein can be used together with ranges or amounts for any of the other elements.

Example 1: Preparation and Isolation of the Extract Secreted by the Strain of *Pseudoalteromonas antarctica* Species with Deposit Number CECT 8690 a) Method of Culture for the Strain of *Pseudoalteromonas antarctica* Species with Deposit Number CECT 8690.

The strain of the *Pseudoalteromonas antarctica* species with deposit number CECT 8690 is cultivated in a bioreactor at 12° C., and a pH=7.0, whose culture medium contains 20 g/L of glucose, 7 g/L of ammonium chloride and a saline solution containing 1 g/L NaCl, 1 g/L magnesium sulfate heptahydrate, 5 g/L disodium phosphate, 2 g/L potassium phosphate, 0.05 g/L calcium chloride, and 0.018 g/L iron sulfate heptahydrate. The inoculum is performed using the required amount of an exponential-state preculture, to have an initial optical density of 0.2 AU (550 nm). The culture lasts 48 hours, having an oxygen concentration controlled at 30% air saturation and stirring with values around 250 rpm.

b) Separation of the Extract Under 10 KDa

The bacteria are separated from the culture broth by centrifugation at 6000 g during 1 h. The elimination of the bacteria is completed with a filtration with membranes having a final pore size of 0.22 μm. Subsequently, the unpurified extract is filtered with a polyethersulfone membrane with a sieve of 10 KDa, and the product of interest permeates across the membrane.

Example 2: Quantification of the Protein Concentration in the Extract Under 10 KDa of *Pseudoalteromonas antarctica* Species with Deposit Number CECT 8690

The concentration values of the extract under 10 KDa purified according to example 1, used in the examples 3 to 14 is the total protein concentration measured with the bicinchoninic acid method, and the instructions provided by the supplier of the kit used (Pierce® BCA Protein Assay Kit, 23227).

The measured total protein concentration of the extract under 10 KDa obtained according to example 1, is 361.55 μg/ml.

Example 3: Chromatographic Analysis SE-HPLC-UV

A solution of the product obtained according to example 1 at 250 μg/ml is prepared and analyzed by HPLC-UV. 100 μl are injected in a High Performance Liquid Chromatography (HPLC) LC20A SHIMADZU. The chromatographic column used is TSKGel® G2000SWXL, 5 m, 125 Å, 7.8 mm×30 mm (TOSOH Bioscience) and water with 0.1M phosphate buffer at pH=6.70+0.1M sodium sulfate as eluent.

Under these conditions, the product shows peaks between 10 and 15 minutes, with a mean peak at 10.75 minutes. The molecular weight is calculated using different standards: Albumin from bovine serum (66000 Da), Ribonuclease A from bovine pancreas Type I (13700 Da) and Salicylic Acid (138 Da). The logarithm of the molecular weight is related with the retention time, in order to obtain a lineal correlation. Using this correlation, the product shows a molecular weight between 7714 Da and 178 Da. Also according to this correlation, the residence time of the main peak maximum (10.75 minutes) corresponds to a molecular weight of 4381 Da.

Example 4: Evaluation of the Inhibition of the Human Melanocortin Receptor 5 (MC5R) Promoter on a Transfected Stable Undifferentiated Epithelial Mammary Cell Line (MCF7) Using a Reporter-Gene Assay An undifferentiated epithelial mammary cell line (MCF7) is stably transfected with a plasmid which contains the Firefly Luciferase gene upon a region of the human MC5R promoter. The selected clone 16 of this cell line, MCF7-MC-16, is treated with the extract obtained in accordance with example 1 in order measure the inhibition of the human MC5R promoter.

Thirty thousand MCF7-MC-16 cells per well in Dulbecco's Modified Eagle Medium (DMEM) (High Glucose) supplemented with 10% FBS (fetal bovine serum), 1% penicillin-streptomycin and 1 μg/ml puromicin are seeded in 96-white well plates treated with Poly-L-lysine solution for Luciferase activity measurements. In parallel, thirty thousand MCF7-MC-16 cells per well are seeded in 96-clear well plates treated with Poly-L-lysine solution, as hereinabove mentioned, for the total cell number quantification by crystal violet staining. Cells are seeded 24 h before starting with the treatments and are incubated at 37° C. and 5% $CO_2$ in a $CO_2$ incubator.

The day of the treatment, MCF7-MC-16 cells are washed twice with Dulbecco's Phosphate Buffer (DPBS) with calcium chloride and magnesium chloride, and incubated during 6 h with DMEM High Glucose without phenol red at 37° C., in a $CO_2$ incubator. Then, the cells are treated with the extract of *Pseudoalteromonas antarctica* species with deposit number CECT 8690, obtained according to example 1, at 0.25 μg/mL or 2.5 μg/mL concentrations. As a control for basal activation, cells are incubated with medium alone. Cells were incubated in DMEM High Glucose without phenol red and supplemented with 1% CS-FBS (charcoal-stripped Fetal Bovine Serum) for 16 to 24 h.

After the incubation period, Relative Light Units per second (RLU/sec) produced by the reaction with Firefly Luciferase are measured in the 96-white well plates and the number of total cells/well is determined in the 96-clear well plates.

Luciferase Activity Determination

Firefly Luciferase substrate (Steady-Glo® Luciferase Assay System, Promega) is added to 96-white well plates following the manufacturer's instructions. Briefly, first, the cells are lysed and the Firefly Luciferase substrate is added. After 10-15 min of incubation, luminescence from Firefly Luciferase activity is read. Relative Light Units per second (RLU/sec) produced by the reaction between Firefly Luciferase and its substrate are quantified using a multiplate luminometer (Lumistar®-BMG).

Determination of the Total Cell Number by Crystal Violet Staining Assay 96-clear well plates containing cells are washed with DPBS and are incubated with Crystal Violet solution (0.05% Crystal Violet, 4% Formalin) during 20 min at room temperature. DNA of the cells is stained by Crystal Violet dye solution. Afterwards, Crystal Violet solution is removed and the wells are washed with Milli-Q water. The amount of Crystal Violet dye taken by up by the cells is directly proportional to the number of cells in each well. Finally, when cells are dried for 1-2 hours at room temperature, and a 0.1M HCl solution is added and absorbance read at 630 nm in a Microplate Absorbance Reader (Multiskan™-Thermo Electro Corporation). Firefly luminescence per second (RLU/sec) results are normalized with the total cell number for the tested dose, and the decrease in the induction of human MC5R promoter is calculated respect to the basal control.

TABLE 1

| Product | Tested dose | Relative induction of MC5R promoter vs basal control |
|---|---|---|
| Extract obtained according to example 1 | 0.25 µg/mL | −14.88% |
| Extract obtained according to example 1 | 2.5 µg/mL | −15.72% |

The results show that the extract under 10 KDa of *Pseudoalteromonas antarctica* decreases the induction of human MC5R promoter.

Example 5: Inhibition of the Accumulation of Sebaceous Lipids in Primary Human Sebocytes Using a Lipid Droplets Fluorescence Assay The inhibition of the accumulation of lipids is determined by means of measuring the fluorescence signal of Nile Red in primary human sebocytes in conditioned differentiation medium after treatment with the extract under 10 KDa of *Pseudoalteromonas antarctica* with deposit number CECT 8690, obtained according to example 1.

Human sebocyte cells are seeded on 96-well plates coated with extracellular matrix at 5,000 cells/well in sebocyte growth medium (50% complete growth media with serum and 50% serum-free media) and are incubated during 3 days, in a $CO_2$ incubator (37° C. and 5% $CO_2$).

After incubation, human sebocyte cells are treated either with conditioned differentiation medium (10 nM [$Nle^4$,D-$Phe^7$]-α-Melanocyte Stimulating Hormone, NDP-α-MSH, in sebocyte growth medium) as basal control for lipid accumulation or with the extract under 10 KDa of *Pseudoalteromonas antarctica* species with deposit number CECT 8690, obtained according to example 1, at 0.25 µg/ml and 2.5 µg/ml in conditioned differentiation medium. Each treatment is performed in triplicate and in parallel for lipid accumulation assay and for cell counting. Cells are incubated within the different treatments during 4 days in a $CO_2$ incubator (37° C. and 5% $CO_2$).

In the basal control, differentiated sebocytes are treated with conditioned differentiation medium, which is the condition of maximum differentiation and therefore, maximum lipid accumulation in this sebocyte model.

Quantification of Sebaceous Lipids Accumulation by AdipoRed™ Reagent Assay

Following manufacturer's instructions, the human sebocyte cells for each condition are washed with Phosphate Buffered Saline (PBS) with calcium and magnesium and diluted AdipoRed™ reagent is added. Upon completion of reagent addition, the human sebocyte cells are incubated at room temperature for 15 min. Then, fluorescence of neutral lipids is measured using the FLUOstar™ Galaxy reader with excitation and emission wavelengths of 485 nm and 530 nm, respectively.

Quantification of Cell Density (Cell Number/Ml) by Cell Counting Assay.

Human sebocyte cells are detached from 96-well plates by treatment with trypsin. After collecting the volumes from triplicate samples, detached cells were centrifuged. About 80% of the supernatant was discarded to concentrate the cells for cell counting assay with TC10™ automated cell counter (Biorad).

Then, the fluorescence signal of each condition is normalized by cell density (cells/ml) to obtain normalized values of lipid accumulation. Finally, the percentage of normalized lipid accumulation compared with the basal control is calculated.

The obtained result shows that the extract under 10 KDa of *Pseudoalteromonas antarctica* species with deposit number CECT 8690, obtained according to example 1, decreases the percentage of sebaceous lipids in human sebocyte cultures.

TABLE 3

| Product | Concentration | % Lipid accumulation vs basal control |
|---|---|---|
| Extract obtained according to example 1 | 0.25 µg/mL | 67.98 |
| Extract obtained according to example 1 | 2.5 µg/mL | 64.77 |

Example 6: In Vitro Study of Photoprotection Against a Cytotoxic Dose of Simulated Sun Light Using Adult Human Dermal Fibroblasts Photoprotective efficacy is measured as an increase of the uptake of the vital dye Neutral Red when measured 24-hours after treatment with a cytotoxic dose of simulated sun light.

Adult human dermal fibroblasts are maintained in a culture for 24 hours to produce monolayers in 96-well plates. Then, the cells are pre-incubated with PBS (Phosphate Buffered Saline) for the irradiated control or with the extract under 10 KDa of *Pseudoalteromonas antarctica* species with deposit number CECT 8690, obtained according to example 1, at 2.5 µg/mL, for 1 h in the darkness at 37° C., 5% $CO_2$, humidified air.

Then, the incubated cells are exposed to the irradiation dose of ~30 to 60 $J/cm^2$ at room temperature for 150/180/210 minutes. Other plate is kept in the darkness for the same time and it is used as non-irradiated control. The culture media of the irradiated plates containing the incubated cells are replaced with fresh culture medium, and the plates are left for 24 h of incubation. The cell viability is determined by uptake of Neutral Red, i.e. after an incubation of 2 hours with Neutral Red Solution (Sigma) cells are lysed and the optical density of the cell lysates is measured at 540 nm in a spectrophotometer. Neutral Red is a weak cationic dye that readily penetrates cell membranes by non-diffusion. Neutral Red is accumulated intracellularly in lysosomes of non-damaged cells, and it is little uptaken in damaged or non-viable cells. To calculate the percentage of cell viability, non-treated cells are used as reference. The photoprotective potential of the tested product is calculated as the increase of cell viability of the treated cells respect to non-treated irradiated cells (treated with PBS). The results are shown in table 4.

TABLE 4

| Product | Irradiation time (min) | Increase of cell viability vs control |
|---|---|---|
| Extract obtained according to example 1 | 150 min | 41.7% |
| Extract obtained according to example 1 | 180 min | 99.3% |
| Extract obtained according to example 1 | 210 min | 142.2% |

Example 7: In Vitro Study of Type I Collagen Synthesis on Human Dermal Fibroblasts by Enzyme-Linked Immunosorbent Assay (ELISA)

Adult human dermal fibroblasts are treated with trypsin and 5×10⁴ cells/well are seeded in 48-well plates. After 24 h of incubation at 37° C. in 5% $CO_2$ humidified air, fresh culture media containing the extract under 10 KDa of *Pseudoalteromonas antarctica* species with deposit number CECT 8690, obtained according to example 1, at 12.5 µg/mL, 6.25 µg/mL, 2.5 µg/mL and 1.25 µg/mL are added. Each concentration is tested in triplicate. Non-treated human dermal fibroblasts are seeded as controls in 48-well plates in 6 wells. Human dermal fibroblasts are incubated for additional 48 h at 37° C. in 5% $CO_2$ humidified air. Then, the culture media are collected to be analysed by ELISA.

A standard curve to quantify type I collagen is prepared with type I collagen from calf skin (Sigma) starting from a stock solution of 1 mg/ml. These dilutions are transferred together with the media previously collected to 96-well plates. Standard curve dilutions and the supernatants collected from the cell culture treatments are transferred to 96-well plates. Collagen in the samples and in the standard curve dilutions coats the walls of the 96-well plates at 4° C. in a humidified atmosphere overnight. Then, the well plates are washed three times with Phosphate Buffered Saline (PBS) with 0.05% Tween-20 (Sigma) and blocked for 1 h with a solution of 3% Bovine Serum Albumin (BSA) (Sigma). After blocking, well plates are incubated with anti-collagen type I antibody (Sigma) for 2 h. After this incubation, the secondary antibody (goat anti-mouse IgG-HRP, *Molecular Probes*) is added. Then, the well plates are incubated with phosphatase substrate (OPD, Sigma) for 30 minutes under stirring. The reaction is stopped by adding 3M $H_2SO_4$. The absorbance at 490 nm is read in a microtiter plate reader and collagen concentration is determined using a linear regression of type I collagen standard curve. Results of collagen synthesis increase versus non-treated cells are shown in table 5.

TABLE 5

| Product | Concentration | Increase of type I collagen synthesis vs control |
|---|---|---|
| Extract obtained according to example 1 | 12.5 µg/mL | 128.4% |
| Extract obtained according to example 1 | 6.25 µg/mL | 82.6% |
| Extract obtained according to example 1 | 2.5 µg/mL | 67.8% |
| Extract obtained according to example 1 | 1.25 µg/mL | 59.9% |

Example 8: Study of the In Vitro Inhibition of Lipid Peroxidation by Means of a TBARS Assay Lipid peroxidation is measured using liposomes as a cell membrane model and monitoring fluorescence due to the formation of adducts between MDA (malondialdehyde) and the TBA (thiobarbituric acid) during TBARS assay (thiobarbituric acid reactive substances). Liposomes are treated with the extract under 10 KDa of *Pseudoalteromonas antarctica* species with deposit number CECT 8690, obtained according to example 1, and compared with a basal control in order to study the decrease in lipid peroxidation of liposomes.

Preparation of Liposomes

A solution containing 30 mM soybean phosphatidylcholine (Emulmetik™ 930) dissolved in chloroform:methanol (1:1) is dried under a stream of oxygen-free $N_2$ in order to obtain a thin film. Last traces of solvent are removed under high vacuum for 3 h. Multilamellar vesicles (MLVs) are formed by addition of Tris-NaCl buffer (140 mM NaCl, 20 mM Tris pH=7.4) followed by 5 min stirring to ensure complete suspension. The vesicle suspension is then sonicated to break up the phospholipid vesicles into small unilamellar vesicles (SUVs).

Liposome Peroxidation 1 ml of SUVs suspension is added to test tubes. Then, 40 µl of different concentrations of the extract under 10 KDa of *Pseudoalteromonas antarctica* species are added to different tubes. 40 µl of Tris-NaCl buffer are added as basal control of the peroxidation. The tubes are incubated for 30 min at 37° C., and each concentration is tested in duplicate.

Lipid peroxidation is initiated by the addition of 40 µl of freshly prepared AAPH (2,2'-Azobis(2-amidinopropane)dihydrochloride (270 mM). Then, the tubes are incubated for 1 h at 37° C. and stirred at 100 rpm. The peroxidation is stopped by adding 200 µl of BHT (butylated hydroxytoluene) (4% w/v in ethanol) and freezing the samples at −20° C.

TBARS Assay

Preparation of the calibration curve of MDA: from a solution of MDA obtained by acid hydrolysis of TEP (1,1,3,3-Tetraethoxypropane) (10 mM in $H_2SO_4$ 1%) five tubes are prepared with 0, 0.8, 1.6, 2.4 and 3.2 nmol of MDA respectively. Finally, 500 µl of distilled water and 100 µl of BHT (4% w/v in ethanol) are added to each tube.

For the reaction with TBA, the samples are thawed, 600 µl are taken with pipettes and added to 250 µl of SDS (sodium dodecyl sulfate) (3% w/v). After mixing, 500 µl of freshly prepared TBA (1% w/v in hot water) are added and mixed. Then, 500 µl of HCl 7 mM are added, stirred and incubated in a water bath at 95° C. for 15 min. Finally, the samples are brought to room temperature and 2 ml of 1-Butanol are added. The samples are stirred vigorously and centrifuged for 5 minutes at 1500 rpm.

150 µl per well of the upper phase of each sample are placed in opaque bottom black 96-well plates in duplicate. Fluorescence is measured at the excitation wavelength of 500 nm and an emission wavelength of 530 nm in a multiplate fluorescence reader (model FluoStar™ Galaxy, BMG Labtech GmbH, Offenburg, Germany). Lipid peroxidation is measured by fluorescence measurements, where 100% is the value of the basal control condition.

TABLE 6

| Product | Concentration | Lipid peroxidation vs basal control |
|---|---|---|
| Extract obtained according to example 1 | 2.5 µg/mL | 96.0% |
| Extract obtained according to example 1 | 10 µg/mL | 92.2% |
| Extract obtained according to example 1 | 15.5 µg/mL | 83.7% |

Example 9: Effect of the Extract Under 10 KDa of the *Pseudoalteromonas antarctica* Species with Deposit Number CECT 8690, Obtained According to Example 1, on the MC5R Protein Level in Primary Human Sebocytes Primary human sebocytes are seeded on T25 cm² flasks coated with extracellular matrix (EM) at 150,000 cells for growth medium condition and at 250,000 cells for the rest of conditions in reduced-serum medium. Cells are incubated in a $CO_2$ incubator (37° C. and 5% $CO_2$) during 3 days in sebocytes growth medium.

After incubation, different conditions are assayed: sebocytes in growth medium as a negative control of differentiation, sebocytes in reduced-serum medium as a positive control of differentiation, and sebocytes with the extract under 10 KDa of *Pseudoalteromonas antarctica* species with deposit number CECT 8690, obtained according to example 1, at 0.25 and 2.5 µg/ml in reduced-serum medium.

After the treatment, cells are prepared for immunocytochemistry by Indirect Flow Cytometry.

Samples Preparation for Indirect Flow Cytometry. Immunocytochemistry

Cells are re-suspended to approximately $1\text{-}5\times10^6$ cells/ml in 1 ml of ice cold Phosphate Buffered Saline (PBS), 10% Newborn Calf Serum (NCS), 1% sodium azide. The suspension containing the cells for each condition is divided into two tubes, one tube is stained with primary antibody (Anti-MC5R Receptor Antibody [EPR8386], ABCAM) and secondary antibody (Goat polyclonal secondary antibody to rabbit IgG-H&L (APC), ABCAM) and the other tube is stained only with secondary antibody (secondary antibody control).

The suspensions containing the cells are fixed with 0.5% Formaldehyde (Sigma) in PBS at room temperature in the darkness. Then, the suspensions are washed by centrifugation with ice cold PBS.

Finally, the cells are re-suspended to approximately $0.5\text{-}2.5\times10^6$ cells/ml in 500 µl of ice cold PBS containing 3% BSA and 1% sodium azide. After counting, the suspensions of cells are stored at 4° C. in the darkness, overnight.

Determination of Extracellular MC5R Protein Level by Flow Cytometry

The assay is carried out at least 3 times. The suspensions of cells for each treatment are run through a Flow Cytometer (FACSCanto™ II, BD Biosciences) and 100,000-200,000 events are collected, the number of events depending on each particular assay. The data are analyzed using WinMDI 2.9 Software.

Light-scattered dot plot of morphology (SSC versus FSC) of each sample are represented and a plot region or gate (R1) is drawn to discard cellular debris.

Fluorescence dot plot of APC (fluorochrome) versus FSC (cellular size) of each sample gate (R1) are represented. Comparing each condition with its secondary antibody control, a gate (R2) is drawn to define positive APC cells (MC5R). For each sample the events included within the regions R1±R2 are quantified. The positive MC5R events of each condition are subtracted secondary antibody control.

The MC5R protein level is calculated respect to reduced-serum medium condition. As it is shown in table 7, the extract under 10 KDa of *Pseudoalteromonas antarctica* species with deposit number CECT 8690, obtained according to example 1, decreases the MC5R protein level in primary human sebocytes in serum-reduced medium.

TABLE 7

| Product | Concentration | MC5R protein level respect reduced-serum medium |
|---|---|---|
| Growth medium | — | 43.7 |
| Extract obtained according to example 1 | 0.25 µg/mL | 63.4 |
| Extract obtained according to example 1 | 2.5 µg/mL | 77.2 |

Example 10: Effect on Differentiation Process of Primary Human Sebocytes by the Extract Under 10 KDa of *Pseudoalteromonas antarctica* Species with Deposit Number CECT 8690

Human sebocytes are seeded on T25 cm² flasks coated with extracellular matrix at 250,000 cells/T25 in sebocyte growth medium (50% complete growth media with serum: 50% serum-free media) and are incubated during 3 days, in a $CO_2$ incubator (37° C. and 5% $CO_2$).

After incubation, human sebocyte cells are treated either with basal growth medium as negative control of differentiation, or conditioned differentiation medium (10 nM [Nle⁴, D-Phe⁷]-α-Melanocyte Stimulating Hormone, NDP-α-MSH, in sebocyte growth medium) as positive control of differentiation, or the extract under 10 KDa of *Pseudoalteromonas antarctica* species with deposit number CECT 8690, obtained according to example 1, at 2.5 µg/ml in conditioned differentiation medium. Cells are incubated within the different treatments during 4 days in a $CO_2$ incubator (37° C. and 5% $CO_2$). After 4 days of treatment, cells are prepared to be processed by Flow Cytometry.

Sample Preparation for Flow Cytometry

Human sebocyte cells are washed 3 times by centrifugation at 100 g for 5 min with ice cold PBS, fixed for 10 min at room temperature with 0.5% formaldehyde solution (Sigma) and washed again once with ice cold PBS. Cell pellets are finally re-suspended in ice cold PBS containing 3% Bovine Serum Albumin (BSA) and 1% sodium azide and stored at 4° C. in the darkness overnight.

Analysis of Cell Morphology: Size (Forward Scatter; FSC) and Granularity (Side Scatter; SSC) by Flow Cytometry The assay is carried out at least 3 times. The suspensions containing the cells for each treatment are run through a Flow Cytometer (FACSCanto™ II, BD Biosciences) and 100,000-200,000 events are collected, the number of events depending on each particular assay. At Flow Cytometry technology, FSC (Forward Scatter) is proportional to cell-surface area or cell size and SSC (Side Scatter) is proportional to cell granularity or internal complexity. FSC versus SSC allows to identify specific morphology of different cell types. Morphological changes of sebocytes for each treatment are analyzed using WinMDI 2.9 Software and they represent granularity versus size (SSC vs. FSC). A gate is drawn to discard cellular debris and cell morphology of gated cells is represented with a density plot of SSC versus FSC. Morphological changes are evaluated by setting up orientative axes on the controls of negative and positive differentiation.

A dot plot representation of flow cytometry data is used for the determination of the distribution of events within the plots, Table 8. The number of events in each quadrant is quantified.

TABLE 8

| SSC | Q1 | Q2 |
|-----|----|----|
|     | Q3 | Q4 |
|     |    | FSC |

Table 9 shows one representative experiment of the three independent experiments carried out. In this assay, cells suspensions corresponding with each treatment are run through a Flow Cytometer and 100.000 events are collected. Table 9 shows the number of events in each quadrant of the plot morphological parameters of size vs granularity of sebocytes grown in different culture conditions. Differentiated sebocytes compared with undifferentiated ones show a change in morphology characterized by high granularity levels (increase of Q2) and small cell size (increase Q3 and decrease Q4). Sebocytes treated with the extract obtained according to example 1 show a morphological change of decreasing granularity (decrease of Q2) and increase of cell size similar to undifferentiated sebocytes (decrease Q3 and increase Q4).

TABLE 9

| SSC/FSC global | | | |
|---|---|---|---|
| | Q2 | Q3 | Q4 |
| Undifferentiated sebocytes | 0.5 | 13 | 87 |
| Differentiated sebocytes | 7.6 | 61 | 31 |
| Extract obtained according to example 1 at 2.5 ug/ml | 4.8 | 21 | 75 |

The results in Table 9 show that the extract under 10 KDa of *Pseudoalteromonas antarctica* species with deposit number CECT 8690, obtained according to example 1, maintains some sebocytes undifferentiated in the presence of differentiation conditioned medium.

FIG. 1 shows density plots of morphological parameters of size (FSC-A) and granularity (SSC-A) for sebocytes grown in different culture conditions. Undifferentiated sebocytes show two main cell populations with similar granularity levels but two different sizes. Differentiated sebocytes show a unique cell population characterized by high granularity levels and small cell size. Sebocytes treated with 2.5 µg/ml of the extract obtained according to example 1, show a change in morphology decreasing granularity and increasing cell size similar to undifferentiated sebocytes. The images belong to the same experiment show in Table 9.

Example 11. Study of the Profile of the Gene Expression of Human Epidermal Keratinocytes The number of times that sets of genes significantly increase/decrease is studied, within the gene profile of human epidermal keratinocytes, by treatment with 2.5 µg/ml of the extract under 10 KDa of *Pseudoalteromonas antarctica* species with deposit number CECT 8690, obtained according to example 1, compared to the basal levels in untreated cells (negative control).

Adult human epidermal keratinocytes, HEKa, (Cascade Biologics) are seeded on T25 flasks pretreated with Coating Matrix ($15 \times 10^4$ cells/flask T25). The adult human epidermal keratinocytes are incubated in complete Epilife medium (Epilife™ medium supplemented with EDGS, Cascade Biologics) for 6 days at 37° C. in an atmosphere with 5% $CO_2$. After the incubation, the cells are treated for 24 hours at 37° C. in an atmosphere with 5% $CO_2$ with 2.5 µg/ml of the extract under 10 KDa of *Pseudoalteromonas antarctica* species with deposit number CECT 8690, obtained according to example 1, in complete Epilife medium or complete Epilife medium as a negative control. The incubations and the treatments are carried out in at least 4 biological assays (flasks) for each condition.

After the treatments, the cells are lysed and RNA is extracted and purified from each flask and each condition by means of the RNeasyPlus™ Mini kit (Qiagen). The lysed cells are homogenized and RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 µl of ultrapure water.

The purity, integrity and concentration of the RNA obtained are evaluated by means of spectrophotometry (Nanodrop) and with a bioanalyzer (Agilent Bioanalyzer).

Later, the labeling is carried out and the samples are hybridized in a human gene expression microarray (ASurePrint™ G3, Agilent).

The normalized values obtained with the treatment are compared with the normalized values obtained with the negative control to obtain genes with differential expression. Then, a parametric analysis of the data is carried out by means of the Bioconductor software. The values obtained are then evaluated by means of GSEA (Gene Set Analysis Enrichment) to group together the genes with differential expression in terms of Gene Ontology and Biological Routes.

The obtained results are shown below in Tables 10 to 13, in which the genes are grouped together.

TABLE 10

Genes involved in INFLAMMATION, downregulated by the extract obtained according to example 1

| Symbol | Name | % Fold change |
|---|---|---|
| CCL2 | chemokine (C-C motif) ligand 2 | −35.68 |
| CSF1 | colony stimulating factor 1 (macrophage) | −17.39 |
| CSF3 | colony stimulating factor 3 (granulocyte) | −53.46 |
| IL1A | interleukin 1, alpha | −41.72 |
| IL6 | interleukin 6 | −55.85 |
| IL8 | interleukin 8 | −33.19 |
| TNF | tumor necrosis factor | −14.44 |
| PTGS2 | prostaglandin-endoperoxide synthase 2 (prostaglandin G/H synthase and cyclooxygenase) | −29.67 |

TABLE 11

Genes involved in OXIDATIVE STRESS and/or DETOXIFICATION, upregulated by the extract obtained according to example 1

| Symbol | Name | % Fold change |
|---|---|---|
| CYP1A1 | cytochrome P450, family 1, subfamily A, polypeptide 1 | 88.48 |
| SOD2 | superoxide dismutase 2, mitochondrial | 64.35 |
| ALDH3A1 | aldehyde dehydrogenase 3 family, member A1 | 112.12 |
| ATP7A | ATPase, Cu++ transporting, alpha polypeptide | 28.62 |
| CYP1B1 | cytochrome P450, family 1, subfamily B, polypeptide 1 | 25.71 |
| GCLC | glutamate-cysteine ligase, catalytic subunit | 69.94 |
| GGT6 | gamma-glutamyltransferase 6 | 57.35 |
| GSTM1 | glutathione S-transferase mu 1 | 26.86 |
| NUDT7 | nudix (nucleoside diphosphate linked moiety X)-type motif 7 | 26.05 |

TABLE 12

Genes involved in ANTI-INFLAMMATORY RESPONSE, upregulated by the extract obtained according to example 1

| Symbol | Name | % Fold change |
|---|---|---|
| NLRP10 | NLR family, pyrin domain containing 10 | 35.39 |
| PGLYRP4 | peptidoglycan recognition protein 4 | 54.86 |

TABLE 13

Genes involved in HYDRATION, upregulated by the extract obtained according to example 1

| Symbol | Name | % Fold change |
|---|---|---|
| AQP9 | aquaporin 9 | 51.27 |

Example 12: Study of the Profile of the Gene Expression of Human Sebocytes

The number of times that sets of genes significantly increase/decrease is studied, within the gene profile of human sebocytes, by treatment with 2.5 µg/ml of the extract under 10 KDa of *Pseudoalteromonas antarctica* species with deposit number CECT 8690, obtained according to example 1, compared to the basal levels in untreated cells (negative control).

The human sebocytes (CELPROGEN) are seeded on T25 flasks coated with extracellular matrix (CELPROGEN) (25×$10^4$ cells/flask), and are incubated in Sebocyte growth medium (50% Human Sebocyte complete growth media and 50% Human Sebocyte serum free media, CELPROGEN) for 3 days at 37° C. in an atmosphere with 5% $CO_2$. After 3 days, serum is reduced from the culture and Sebocytes growth medium is replaced by reduced-serum medium (5% Human Sebocyte complete growth media and 95% Human Sebocyte serum free media, CELPROGEN) and sebocytes are incubated for 3 days. After the incubation, the cells are treated for 24 hours at 37° C. in an atmosphere with 5% $CO_2$ with 2.5 µg/ml of the extract under 10 KDa of *Pseudoalteromonas antarctica* species with deposit number CECT 8690, obtained according to example 1, in reduced-serum medium or reduced-serum medium as negative control. The incubations and the treatments are carried out in at least 4 biological assays (flasks) for each condition.

After the treatments, the cells are lysed and RNA is extracted and purified from each flask and each condition by means of the RNeasyPlus Mini kit (Qiagen). The lysed cells are homogenized and RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 µl of ultrapure water.

The purity, integrity and concentration of the RNA obtained are evaluated by means of spectrophotometry (Nanodrop) and with a bioanalyzer (Agilent Bioanalyzer).

Later, the labeling is carried out and the samples are hybridized in a human gene expression microarray (ASurePrint G3, Agilent).

The normalized values obtained with the treatment are compared with the normalized values obtained with the negative control to obtain genes with differential expression. Then, a parametric analysis of the data is carried out by means of the Bioconductor software. The values obtained are then evaluated by means of GSEA (Gene Set Analysis Enrichment) to group together the genes with differential expression in terms of Gene Ontology and Biological Routes.

The obtained results are shown below in Tables 14 to 17, in which the genes are grouped together.

TABLE 14

Genes involved in INFLAMMATION, downregulated by the extract obtained according to example 1

| Symbol | Name | % Fold change |
|---|---|---|
| CCL2 | chemokine (C-C motif) ligand 2 | −62.13 |
| LTB | lymphotoxin beta (TNF superfamily, member 3) | −46.26 |
| TLR2 | toll-like receptor 2 | −25.10 |
| TNF | tumor necrosis factor | −36.57 |
| CXCR7 | chemokine (C—X—C motif) receptor 7 | −30.19 |
| SAA1 | serum amyloid A1 | −55.36 |
| IL8 | interleukin 8 | −28.03 |
| CXCL1 | chemokine (C—X—C motif) ligand 1 (melanoma growth stimulating activity, alpha) | −50.97 |
| CXCL5 | chemokine (C—X—C motif) ligand 5 | −45.32 |

TABLE 15

Genes involved in SEBOCYTE PROLIFERATION AND DIFFERENTIATION, downregulated by the extract obtained according to example 1

| Symbol | Name | % Fold change |
|---|---|---|
| BORA | bora, aurora kinase A activator | −24.02 |
| CCNB1 | cyclin B1 | −22.58 |
| CCND3 | cyclin D3 | −25.22 |
| WNT5A | wingless-type MMTV integration site family, member 5A | −20.85 |

TABLE 16

Genes involved in OXIDATIVE STRESS AND DNA-REPAIR, upregulated by the extract obtained according to example 1

| Symbol | Name | % Fold change |
|---|---|---|
| CYP1A1 | cytochrome P450, family 1, subfamily A, polypeptide 1 | 62.62 |
| GADD45A | growth arrest and DNA-damage-inducible, alpha | 36.36 |

TABLE 17

Genes involved in RETINOID METABOLISM, upregulated by the extract obtained according to example 1. The Retinoid Metabolism is related with the production of sebum in the skin

| Symbol | Name | % Fold change |
|---|---|---|
| RLBP1 | retinaldehyde binding protein 1 | 83.26 |
| STRA6 | stimulated by retinoic acid 6 | 47.36 |

Example 13: Preparation of a Cosmetic Composition of the Extract Under 10 KDa of *Pseudoalteromonas antarctica* Species with Deposit Number CECT 8690

In a suitable vessel, the ingredients of Phase A are dissolved in water under turbine stirring, until a total dispersion is achieved. Subsequently, Phase B, Novemer EC2 [INCI: WATER (AQUA), SODIUM ACRYLATES, BEHENETH 25 METHACRYLATE, CROSSPOLYMER, HYDROGENATED POLYDECENE, LAURYL GLUCOSIDE] is added little by little, under turbine stirring.

Then, a water solution of the extract under 10 KDa of *Pseudoalteromonas antarctica* species obtained according to example 1 at a concentration of 62.5 µg/ml, and sodium salicylate, are added (Phase C).

The list of ingredients is in Table 18.

TABLE 18

| INGREDIENT (INCI name) | % weight | Phase |
|---|---|---|
| WATER (AQUA) | 90.50 | A |
| Water solution of the extract obtained according to example 1 | 5.00 | C |
| SODIUM SALICYLATE | 0.01 | C |
| WATER (AQUA) | 1.4 | B |
| SODIUM ACRYLATES/BEHENETH 25 METHACRYLATE/CROSSPOLYMER | 0.83 | B |
| HYDROGENATED POLYDECENE | 0.68 | B |
| LAURYL GLUCOSIDE | 0.09 | B |
| PHENOXYETHANOL | 0.86 | A |
| METHYLPARABEN | 0.19 | A |
| PROPYLPARABEN | 0.10 | A |
| ETHYLPARABEN | 0.05 | A |
| DISODIUM EDTA | 0.30 | A |

Example 14: Preparation of a Cosmetic Composition of the Extract Under 10 KDa of *Pseudoalteromonas antarctica* Species with Deposit Number CECT 8690

In a suitable vessel, the ingredients of Phase A are dissolved in water under turbine stirring, until a total dispersion is achieved. The extract under 10 KDa of *Pseudoalteromonas antarctica* species obtained according to example 1 is added to Phase A as a water solution of the extract at a concentration of 250 µg/ml.

Subsequently, the components of Phase B are added little by little, under turbine stirring, until total dispersion. The pH is adjusted at 6.3-6.8.

The list of ingredients is in Table 19.

TABLE 19

| INGREDIENT (INCI name) | % weight | PHASE |
|---|---|---|
| WATER (AQUA) | 94.74 | A |
| Extract obtained according to example 1 | 0.75 | A |

TABLE 19-continued

| INGREDIENT (INCI name) | % weight | PHASE |
|---|---|---|
| WATER (AQUA) | 1.41 | B |
| SODIUM ACRYLATES/BEHENETH-25 METHACRYLATE/CROSSPOLYMER | 0.83 | B |
| HYDROGENATED POLYDECENE | 0.68 | B |
| LAURYL GLUCOSIDE | 0.09 | B |
| PHENOXYETHANOL | 0.86 | A |
| METHYLPARABEN | 0.19 | A |
| PROPYLPARABEN | 0.10 | A |
| ETHYLPARABEN | 0.05 | A |
| DISODIUM EDTA | 0.30 | A |
| SODIUM SALICYLATE | 0.01 | A |

Example 15: In Vivo Study for the Efficacy of the Extract Under 10 KDa of *Pseudoalteromonas antarctica* Species with Deposit Number CECT 8690 in Oily Skin of Asiatic Skin Type Volunteers The study is carried out in 20 Asiatic female volunteers between 20 and 35 years old. Volunteers apply the composition of the example 14, in the face and forehead twice a day (morning and night) for 28 days. The study measures the number and surface of active follicles secreting sebum, spots, at the initial time before the use of the composition of example 14 and at day 28. The subjects served as their own references comparing their result obtained at day 28 with the result obtained at the initial time. The efficacy is measured with Sebutape®, a sebum sensitive adhesive film. The results are shown in Table 20.

TABLE 20

|  | VARIATION (%) (T + 28 days − T0)/T0 |
|---|---|
| Number of spots | −9.5% |
| Total Surface of the spots | −27.2% |

The results show a mean decrease of 9.5% of active follicles secreting sebum and a mean decrease of 27.2% of surface of active follicles secreting sebum in 20 volunteers.

Example 16: Preparation of a BB Cream Composition of the Extract Under 10 KDa of *Pseudoalteromonas antarctica* Species with Deposit Number CECT 8690

In a suitable vessel, the ingredients of Phase A [INCI: WATER, METHYL GLUCETH-20, ALLANTOIN, SODIUM HYDROXIDE, DISODIUM EDTA, POTASSIUM SORBATE] are dissolved under turbine stirring and the mixture is heated at 50° C. until a total dispersion is achieved.

Subsequently, Phase B1 [INCI: CARBOPOL®ULTREZ 20 ACRYLATES/C10-30 ALKYL ACRYLATE CROSSPOLYMER], left to wet and then dispersed, and Phase B2 [INCI: XANTHAN GUM] is added, left to wet and then dispersed also.

Next, the ingredients of Phase C are added [INCI: CI 77891 & AQUA & GLYCERIN & XANTHAN GUM & SODIUM CITRATE, CI77492 & AQUA& GLYCERIN & XANTHAN GUM & SODIUM CITRATE, CI 77491 & AQUA & GLYCERIN & XANTHAN GUM & SODIUM CITRATE, CI77499 & AQUA & GLYCERIN & XANTHAN GUM & SODIUM CITRATE] and allowed to homogenize the color itself by stirring. When the mixture is homogeneous, the temperature is raised to 75° C.

Into another beaker, Phase D ingredients [INCI: ISOPROPYL ISOSTEARATE, CAPRYLIC CAPRIC TRIGLYCERIDE, METHYL GLUCOSE SESQUISTEARATE, BEHENYL ALCOHOL, DIMETHICONE, PEG-20 METHYL GLUCOSE SESQUISTEARATE, PHENOXYETHANOL, VITAMIN E ACETATE] are weighed and the mixture is heated at 80° C.

When the respective temperatures are reached, the emulsion is made by adding slowly Phase D mixture to the mixture of the Phases A, B1, B2 and C under stirring, first at 600 rpm and then one minute with a turax at 10000 rpm.

When the mixture has cooled to 65° C., Phase E [INCI: MICA, BORON NITRIDE, MICA] is added. Then, a water solution of the extract under 10 KDa of *Pseudoalteromonas antarctica* species obtained according to example 1 at a concentration of 62.5 μg/ml, and sodium salicylate, (Phase F) [INCI: WATER, *PSEUDOALTEROMONAS* FERMENT EXTRACT, SODIUM SALICYLATE], and Phase G [INCI: FRAGRANCE] are added to the previous mixture when the bulk is at 30° C.

The list of ingredients is in Table 21.

TABLE 21

| INGREDIENT (INCI name) | % weight | Phase |
|---|---|---|
| WATER | 56.95 | A |
| METHYL GLUCETH-20 | 5 | A |
| ALLANTOIN | 0.2 | A |
| SODIUM HYDROXIDE | 0.15 | A |
| DISODIUM EDTA | 0.1 | A |
| POTASSIUM SORBATE | 0.05 | A |
| CARBOPOL ® ULTREZ 20 ACRYLATES/C10-30 ALKYL ACRYLATE CROSSPOLYMER | 0.1 | B |
| XANTHAN GUM | 0.3 | B |
| CI 77891 & AQUA & GLYCERIN & XANTHAN GUM & SODIUM CITRATE | 6 | C |
| CI77492 & AQUA& GLYCERIN & XANTHAN GUM & SODIUM CITRATE | 0.6 | C |
| CI 77491 & AQUA & GLYCERIN & XANTHAN GUM & SODIUM CITRATE | 0.4 | C |
| CI77499 & AQUA & GLYCERIN & XANTHAN GUM & SODIUM CITRATE | 0.2 | C |
| ISOPROPYL ISOSTEARATE | 5.9 | D |
| CAPRYLIC CAPRIC TRIGLYCERIDE | 4.1 | D |
| METHYL GLUCOSE SESQUISTEARATE | 3.4 | D |
| BEHENYL ALCOHOL | 3 | D |
| DIMETHICONE | 2 | D |
| PEG-20 METHYL GLUCOSE SESQUISTEARATE | 1.6 | D |
| PHENOXYETHANOL | 0.5 | D |
| VITAMINE E ACETATE | 0.2 | D |
| MICA | 3 | E |
| BORON NITRIDE | 3 | E |
| MICA | 1 | E |
| WATER, PSEUDOALTEROMONAS FERMENT EXTRACT, SODIUM SALICYLATE | 2 | F |
| FRAGRANCE | 0.25 | G |

Example 17: Preparation of a BB Cream Placebo Composition

The composition is prepared according to the instructions of example 16, but without the *Pseudoalteromonas antarctica* extract, with the following ingredients included in Table 22.

TABLE 22

| INGREDIENT (INCI name) | % weight | Phase |
|---|---|---|
| DEIONIZED WATER | 58.95 | A |
| METHYL GLUCETH-20 | 5 | A |

TABLE 22-continued

| INGREDIENT (INCI name) | % weight | Phase |
|---|---|---|
| ALLANTOIN | 0.2 | A |
| SODIUM HYDROXIDE | 0.15 | A |
| DISODIUM EDTA | 0.1 | A |
| POTASSIUM SORBATE | 0.05 | A |
| CARBOPOL ®ULTREZ 20 ACRYLATES/C10-30 ALKYL ACRYLATE CROSSPOLYMER | 0.1 | B |
| XANTHAN GUM | 0.3 | B |
| CI 77891 & AQUA & GLYCERIN & XANTHAN GUM & SODIUM CITRATE | 6 | C |
| CI77492 & AQUA& GLYCERIN & XANTHAN GUM & SODIUM CITRATE | 0.6 | C |
| CI 77491 & AQUA & GLYCERIN & XANTHAN GUM & SODIUM CITRATE | 0.4 | C |
| CI77499 & AQUA & GLYCERIN & XANTHAN GUM & SODIUM CITRATE | 0.2 | C |
| ISOPROPYL ISOSTEARATE | 5.9 | D |
| CAPRYLIC CAPRIC TRIGLYCERIDE | 4.1 | D |
| METHYL GLUCOSE SESQUISTEARATE | 3.4 | D |
| BEHENYL ALCOHOL | 3 | D |
| DIMETHICONE | 2 | D |
| PEG-20 METHYL GLUCOSE SESQUISTEARATE | 1.6 | D |
| PHENOXYETHANOL | 0.5 | D |
| VITAMINE E ACETATE | 0.2 | D |
| MICA | 3 | E |
| BORON NITRIDE | 3 | E |
| MICA | 1 | E |
| FRAGRANCE | 0.25 | F |

Example 18: In Vivo Study for the Efficacy of the Extract Under 10 KDa of *Pseudoalteromonas antarctica* Species with Deposit Number CECT 8690 in the Long Lasting Mattifying Effect of a BB Cream The study is carried out in 22 Caucasian female volunteers between 18 and 42 years old. Volunteers apply the composition of the example 16, in one half-face and the placebo (example 17) in the other half-face. After a single product application the skin shininess is measured, at the initial time before the use of the composition, immediately after the product application and 2 hours and 8 hours after product application. The efficacy is measured with Skin-Glossymeter® GL 200. The results are shown in Table 23.

TABLE 23

| | VARIATION (%) | |
|---|---|---|
| | Active (TX hours − T0)/T0 | Placebo (TX hours − T0)/T0 |
| T Immediately after | −28.31% | −13.01% |
| T 2 h | −25.18% | −14.61% |
| T 8 h | −14.95% | 7.17% |

Measurements immediately after product application show that the decrease of skin shininess is higher with active cream (the composition of the example 16, with the extract under 10 KDa of *Pseudoalteromonas antarctica* species with deposit number CECT 8690) than with placebo cream. A similar result is found after 2 hours. However, after 8 hours of product application the active cream is able to decrease the skin shininess while with placebo cream the skin shininess increases.

Example 19: In Vivo Study with the Bacterial Extracellular Product Secreted by the Strain of the Species *Pseudoalteromonas antarctica* with Deposit Number CECT 8690, Obtained According to Example 1; Test for Efficacy for the Treatment of Oily Skin in Caucasian Skin Type Volunteers The study was carried out during 28 days with measurements at initial time, after 14 days and after 28 days. 20 volunteers were included being Caucasian females between 20 and 35 years old. Subjects applied the gel-cream of the example 13, twice a day (morning and night). The subjects served as their own reference and results obtained at different times were compared with those obtained at initial time. The efficacy of the product was assessed by:

Measurements with Sebumeter® to determine the sebum rate of the skin on both sides of the nose; results are shown in table 24.

Digital photographs with Epiflash™ for image analysis of pores on both sides of the nose; results are shown in table 25.

Digital photographs with Visia-CR™ for image analysis of the skin shininess on the forehead; results are shown in table 26.

TABLE 24

Percentage variations respect initial time of the total amount of sebum at 14 and 28 days

| | VARIATIONS (%)* | |
|---|---|---|
| | (T + 14 days − T0)/T0 | (T + 28 days − T0)/T0 |
| Sebum rate | −8.4% | −9.4% |

*calculated on the average values

The results show a decrease in sebum rate of 8.4% after 14 days of product application. After 28 days, the reduction in sebum rate is up to 9.4%.

TABLE 25

Percentage variations respect initial time of the number and total surface of spots at 14 and 28 days

| | VARIATIONS (%)* | |
|---|---|---|
| | (T + 14 days − T0)/T0 | (T + 28 days − T0)/T0 |
| Number of pores | −20.5% | −18.0% |
| Total area of pores | −18.8% | −18.7% |

*calculated on the average values

The results show a reduction of number of pores of 20.5% after 14 days and 18.0% after 28 days of product application. In relation to total area of pores, reductions of 18.8% and 18.7% were found after 14 and 28 days of product application, respectively.

TABLE 26

Percentage variations respect initial time of the skin shininess on the forehead, at 14 and 28 days

| | VARIATIONS (%)* | |
|---|---|---|
| | (T + 14 days − T0)/T0 | (T + 28 days − T0)/T0 |
| Shininess intensity | −17.0% | −27.3% |

*calculated on the average values

The results show a reduction of skin shininess intensity of 17% after 14 days of treatment. After 28 days of product application the reduction was up to 27.3% of skin shininess intensity.

The invention claimed is:

1. A method of treatment and/or care of the skin mucous membranes and/or hair of a subject, comprising administering a cosmetically or dermopharmaceutically effective quantity of an extracellular extract of molecular weight less than 10,000 Da produced by fermentation of a strain of *Pseudoalteromonas antarctica* species and filtration to eliminate molecules of molecular weight greater than 10,000 Da, to the skin, mucous membranes and/or hair of the subject.

2. The method according to claim 1, wherein the treatment is a treatment of inflammation, skin cancer, comedones, milia, acne, seborrhea, seborrheic dermatitis, hidradenitis suppurativa or photoprotection of the skin.

3. The method according to claim 1, wherein the treatment and/or care is a treatment of reduction of the sebum amount in the skin and/or hair, treatment of skin aging, treatment of skin wrinkles, treatment of skin firming, hindering or delaying loss of skin firmness, and/or for hair hygiene.

4. The method according to claim 1, wherein the treatment and/or care is for the maintenance or improvement of hydration of the skin.

5. The method according to claim 1, wherein the treatment and/or care inhibits the receptor MC5R and/or stimulates collagen synthesis.

6. The method according to claim 1, wherein the molecular weight of the extracellular extract is greater than 50 Da.

7. The method according to claim 1, wherein the strain of *Pseudoalteromonas antarctica* species is a strain with deposit number CECT 8690.

8. The method according to claim 1, wherein the molecular weight of the extracellular extract is between 100 Da and 8,000 Da.

9. The method of claim 1, wherein the molecular weight of the extracellular extract is between 150 Da and 6,000 Da.

10. The method of claim 1, wherein the molecular weight of the extracellular extract is between 300 Da and 5,000 Da.

11. A cosmetic or dermopharmaceutical composition comprising a cosmetically or dermopharmaceutically effective quantity of an extracellular extract of molecular weight less than 10,000 Da produced by fermenting a strain of *Pseudoalteromonas antarctica* species and filtration to eliminate molecules of molecular weight greater than 10,000 Da, and at least one cosmetically and/or dermopharmaceutically acceptable excipient, adjuvant and/or ingredient.

12. The cosmetic or dermopharmaceutical composition, according to claim 11, wherein the extracellular extract is incorporated into a cosmetically or dermopharmaceutically acceptable delivery system or sustained release system selected from the group consisting of liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules, nanocapsules, microemulsions and nanoemulsions or is adsorbed on a solid organic polymer or solid mineral support selected from the group consisting of talc, bentonite, silica, starch and maltodextrin.

13. The cosmetic or dermopharmaceutical composition, according to claim 11, wherein the composition is presented in a formulation selected from the group consisting of multiple emulsions, liquid crystals, anhydrous compositions, oils, balsams, foams, aqueous or oily lotions, aqueous or oily gels, creams, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils, sprays and aerosols.

14. The cosmetic or dermopharmaceutical composition according to claim 11, which is incorporated into a fabric, non-woven fabric or medical device.

15. The cosmetic or dermopharmaceutical composition, according to claim 11, wherein said excipient, adjuvant and/or ingredient is selected from the group consisting of agents which diminish the sebum production, anti-seborrheic agents, mattifying agents, anti-acne agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, other anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of lipids and components of the stratum corneum, ceramides, fatty acids, agents that inhibit collagen degradation, agents that inhibit matrix metalloproteinases, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, binding agents, lipolytic agents or agents stimulating lipolysis, adipogenic agents, agents modulating PGC-1α expression, agents modulating the activity of PPARγ, agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents which improve dermal-epidermal junction, agents inducing hair growth, hair growth inhibiting or retardant agents, hair loss retardant agents, preservatives, perfumes, odor absorbents and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

16. The cosmetic or dermopharmaceutical composition according to claim 11, wherein the extracellular extract is between 0.000001% by weight and 5% by weight of the composition.

17. The cosmetic or dermopharmaceutical composition according to claim 11, wherein the extracellular extract is between 0.0001% by weight and 5% by weight of the composition.

18. The cosmetic or dermopharmaceutical composition according to claim 11, wherein said excipient, adjuvant and/or ingredient comprises an agent which increases percutaneous absorption selected from the group consisting of dimethyl sulfoxide, dimethylacetamide, dimethylformamide, surfactants, azone (1-dodecylazacycloheptane-2-one), alcohol, urea, ethoxydiglycol, acetone, propylene glycol and polyethylene glycol.

19. The cosmetic or dermopharmaceutical composition according to claim 11, wherein the composition comprises:
  between 0.0000000001% by weight and 20% by weight of the extracellular extract;
  between 0.1% by weight and 20% by weight of a humectant selected from the group consisting of glycerin, propylene glycol, butylene glycol, pentylene glycol, caprylyl glycol, lactic acid, urea, and sodium hyaluronate;
  between 0.1% by weight and 20% by weight of an emollient or skin conditioning compound selected from the group consisting of dimethicone, glyceryl stearate, caprylic/capric triglyceride, cetearyl alcohol, lecithin, $C_{12-15}$ alkyl benzoate, squalane, lanolin, behenyl alcohol, tocopheryl acetate, panthenol, *Butyrospermum parkii* butter, retinyl palmitate, and retinol; and
  between 0.1% by weight and 20% by weight of a surfactant selected from the group consisting of xanthan gum, sodium laureth sulfate, stearic acid, Polysorbate 20, Polysorbate 80, stearyl alcohol, cetyl alcohol, Steareth-2, Ceteareth-20, and cocamidopropyl betaine.

* * * * *